United States Patent
Lowman et al.

(10) Patent No.: US 7,348,154 B2
(45) Date of Patent: Mar. 25, 2008

(54) IGF BINDING PROTEINS

(75) Inventors: Henry Lowman, El Granada, CA (US); Samantha Lien, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 11/525,458

(22) Filed: Sep. 21, 2006

(65) Prior Publication Data

US 2007/0020698 A1    Jan. 25, 2007

Related U.S. Application Data

(62) Division of application No. 10/936,059, filed on Sep. 8, 2004, now Pat. No. 7,192,738.

(60) Provisional application No. 60/508,345, filed on Oct. 3, 2003.

(51) Int. Cl.
    *G01N 33/53*     (2006.01)
    *C07K 14/00*     (2006.01)

(52) U.S. Cl. ........................... 435/7.1; 530/351

(58) Field of Classification Search ........... 435/7.1; 530/351
See application file for complete search history.

(56) References Cited

U.S. PATENT DOCUMENTS

| | | |
|---|---|---|
| 5,077,276 A | 12/1991 | Ballard et al. |
| 5,164,370 A | 11/1992 | Ballard et al. |
| 5,212,074 A | 5/1993 | Kiefer et al. |
| 5,258,287 A | 11/1993 | Baxter et al. |
| 5,328,891 A | 7/1994 | Baxter et al. |
| 5,470,828 A | 11/1995 | Ballard et al. |
| 5,714,460 A | 2/1998 | Gluckman et al. |
| 5,840,673 A | 11/1998 | Buckbinder et al. |
| 5,973,115 A | 10/1999 | Clemmons et al. |
| 6,004,775 A | 12/1999 | Shimasaki et al. |
| 6,025,465 A | 2/2000 | Kiefer et al. |
| 6,121,416 A | 9/2000 | Clark et al. |
| 6,251,865 B1 | 6/2001 | Clark et al. |

(Continued)

FOREIGN PATENT DOCUMENTS

EP     0 230 869     8/1987

(Continued)

OTHER PUBLICATIONS

Payet et al. Jul. 2003; Amino-and carboxyl-terminal fragments of insulin-like growth factor (IGF) binding protein-3 cooperate to bind IGFs with high affinity and inhibit IGF receptor interactions. Endocrinology 144(7): 2797-2806.*

(Continued)

*Primary Examiner*—Karen Cochrane Carlson
(74) *Attorney, Agent, or Firm*—Janet E. Hasak, Esq.; Ginger R. Dreger, Esq.; Heller Ehrman LLP

(57) ABSTRACT

IGFBP-3 fusion proteins are provided that are useful, for example, in cell-based assays, as IGF antagonists, and in mapping IGF-I and IGF-II binding sites on other molecules such as wild-type IGFBP-3 and IGF agonist peptides identified by phage display. Methods for making such fusion proteins are also provided.

9 Claims, 8 Drawing Sheets

U.S. PATENT DOCUMENTS

| | | | |
|---|---|---|---|
| 6,369,029 | B1 | 4/2002 | Andress et al. |
| 6,391,588 | B1 | 5/2002 | Andress et al. |
| 6,410,335 | B1 | 6/2002 | Pollak et al. |
| 6,417,330 | B1 | 7/2002 | Mascarenhas et al. |
| 6,489,294 | B1 | 12/2002 | Andress et al. |
| 6,500,635 | B1 | 12/2002 | Kiefer |
| 7,192,738 | B2 * | 3/2007 | Lowman et al. ............ 435/69.1 |
| 2001/0018190 | A1 | 8/2001 | Pollak et al. |
| 2002/0072589 | A1 | 6/2002 | Mascarenhas et al. |
| 2003/0059430 | A1 | 3/2003 | Mascarenhas |
| 2003/0082744 | A1 | 5/2003 | Kiefer |
| 2003/0092631 | A1 | 5/2003 | Deshayes et al. |
| 2003/0161829 | A1 | 8/2003 | Mascarenhas |

FOREIGN PATENT DOCUMENTS

| | | |
|---|---|---|
| EP | 0 294 021 | 12/1988 |
| EP | 0 375 438 | 6/1990 |
| EP | 0 369 943 | 9/1990 |
| EP | 0 546 053 | 6/1993 |
| EP | 1 295 939 | 3/2003 |
| WO | WO 89/08667 | 9/1989 |
| WO | WO 89/09268 | 10/1989 |
| WO | WO 89/09792 | 10/1989 |
| WO | WO 90/00569 | 1/1990 |
| WO | WO 92/03152 | 3/1992 |
| WO | WO 92/03469 | 3/1992 |
| WO | WO 92/03470 | 3/1992 |
| WO | WO 92/03471 | 3/1992 |
| WO | WO 92/12243 | 7/1992 |
| WO | WO 92/14834 | 9/1992 |
| WO | WO 93/23067 | 11/1993 |
| WO | WO 94/22466 | 10/1994 |
| WO | WO 97/09998 | 3/1997 |
| WO | WO 99/32620 | 7/1999 |
| WO | WO 99/63086 | 12/1999 |
| WO | WO 00/23469 | 4/2000 |
| WO | WO 00/35473 | 6/2000 |
| WO | WO 01/72771 | 10/2001 |
| WO | WO 01/75064 | 10/2001 |
| WO | WO 01/87238 | 11/2001 |
| WO | WO 02/34916 | 5/2002 |
| WO | WO 02/098914 | 12/2002 |
| WO | WO 03/006029 | 1/2003 |
| WO | WO 03/025121 | 3/2003 |
| WO | WO 03/052079 | 6/2003 |
| WO | WO 03/068160 | 8/2003 |

OTHER PUBLICATIONS

Andress and Birnbaum, "A novel human insulin-like growth factor binding protein secreted by osteoblast-like cells" *Biochim. Biophys. Res Com.* 176:213-218 (1991).

Angelloz-Nicoud et al., "Prostate carcinoma (PC-3) cell proliferation is stimulated by the 22-25-kDa proteolytic fragment (1-160) and inhibited by the 16-kDa fragment (1-95) of recombinant human insulin-like growth factor binding protein-3" *Growth Hormone & IGP Research* 8:71-75 (1990).

Bach and Rechler., "Insulin-Like Growth Factor Binding Proteins." *Diabetes Reviews.* 3(1):38-61 (1995).

Bagley et al., "A key functional role for the insulin-like growth factor 1 N-terminal pentapeptide" *Biochemical Journal* 259(3):665-671 (May 1, 1989).

Bar et al., "Tissue Localization of Perfused Endothelial Cell IGF Binding Protein is Markedly Altered by Association with IGF-I." *Endocrinology.* 127(6):3243-3245 (1990).

Baxter & Martin, "Binding Proteins for Insulin-Like Growth Factors in Adult Rat Serum. Comparison With Other Human and Rat Binding Proteins" *Biochem. & Biophys. Res. Comm.* 147(1):408-415 (1987).

Baxter et al., "Growth Hormone-Dependent Insulin-Like Growth Factor (IGF) Binding Protein from Human Plasma Differs from Other Human IGF Binding Proteins" *Biochem. & Biophys. Res. Comm.* 139(3):1256-1261.

Baxter et al., "Recommendations for nomenclature of the insulin-like growth factor binding protein superfamily" *Endocrinology* 139(10):4036 (Oct. 1998).

Baxter et al., "Structural determinants for binary and ternary complex formation between insulin-like growth factor-I (IGF-I) and IGF binding protein-3" *Journal of Biological Chemistry* 267(1):60-65 (Jan. 5, 1992).

Baxter, R., "The Insulin-Like Growth Factors and Their Binding Proteins" *Comp. Biochem. Physiol.* 91B(2):229-235 (1988).

Bayne et al., "Structural Analogs of Human Insulin-Like Growth Factor I with Reduced Affinity for Serum Binding Proteins and the Type 2 Insulin-Like Growth Factor Receptor." *J. Bio. Chem.* 263:6233-6239 (1988).

Bayne et al., "The C Region of Human Insulin-Like Growth Factor (IGF) I is Required for High Affinity Binding to the Type 1 IGF Receptor." *J. Bio. Chem.* 264(19): 11004-11008 (1988).

Bayne et al., "The Roles of Tyrosines 24, 31, and 60 in the High Affinity Binding of Insulin-Like Growth Factor-I to the Type I Insulin-Like Growth Factor Receptor." *J. Bio. Chem.* 265(26):15648-15652 (Sep. 15, 1990).

Bernard et al., "The amino-terminal region of insulin-like growth factor binding protein-3, 1 95 IGFBP-3, induces apoptosis of MCF-7 breast carcinoma cells" *Biochem. & Biophys. Res. Comm.* 293:55-60 (2002).

Binkert et al., "Cloning, sequence analysis and expression of a cDNA encoding a novel insulin-like growth factor binding protein (IGFBP-2)" *EMBO Journal* 8:2497-2502 (1989).

Blundell et al., "Insulin-Like Growth Factor: A Model for Tertiary Structure Accounting for Immunoreactivity and Receptor Binding." *Proc. Natl. Acad. Sci. USA* 75(1):180-184 (Jan. 1978).

Blundell et al., "Tertiary Structures, Receptor Binding, and Antigenicity of Insulinlike Growth Factors." *Federation Proc.* 42:2592-2597 (1983).

Brewer et al., "Cloning, Characterization, and Expression of a Human Insulin-Like Growth Factor Binding Protein" *Biochem. & Biophys. Res. Comm.* 152(3):1289-1297 (1988).

Brinkman et al., "Isolation and characterization of a cDNA encoding the low molecular weight insulin-like growth factor binding protein (IBP-1)" *The EMBO J.* 7:2417-2423 (1988).

Campbell et al., "Insulin-like Growth Factor-binding Protein-3 Binds Fibrinogen and Fibrin" *Journal of Biological Chemistry* 274:30215-30221 (1999).

Campbell et al., "Plasminogen binds the heparin-binding domain of insulin-like growth factor-binding protein-3" *Am. J. Physiol.* 275:E321-E231 (1998).

Carter, "American Chemical Society Symposium Series No. 427" *Protein Purification: From Molecular Mechanisms to Large-Scale Processes.*, Ladisch et al., Eds., Chapter 13, pp. 181-193 (1990).

Cascieri et al., "Mutants of Human Insulin-Like Growth Factor I with Reduced Affinity for the Type 1 Insulin-Like Growth Factor Receptor." *Biochemistry* 27(9):3229-3233 (May 3, 1988).

Cascieri et al., "Structural Analogs of Human Insulin-Like Growth Factor (IGF) I with Altered Affinity for Type 2 IGF Receptors." *J. Bio. Chem.* 264:2199-2202 (1989).

Chen et al., "A highly sensitive and specific assay for determination of IGF-I bioactivity in human serum" *Am. J. Physiol. Endocrinol. Metab.* 284:E1149-E1155 (2003).

Chernausek et al., "Proteolytic cleavage of insulin-like growth factor binding protein 4 (IGFBP-4). Localization of cleavage site to non-homologous region of native IGFBP-4" *Journal of Biological Chemistry* 270(19):11377-11382 (May 12, 1995).

Clark and Robinson, "Up and down the growth hormone cascade" *Cytokine & Growth Factor Reviews* 7(1):65-80 (Jun. 1996).

Clemmons et al., "Competition for Binding to Insulin-Like Growth Factor (IGF) Binding Protein-2, 3, 4, and 5 by the IGFs and IGF Analogs." *Endocrinology.* 131(2):890-895 (Aug. 1992).

Clemmons et al., "Discrete Alterations of the Insulin-Like Growth Factor I Molecule Which Alter Its Affinity for Insulin-Like Growth Factor-Binding Proteins Result in Changes in Bioactivity." *J. Bio. Chem.* 265(21):12210-12216 (1990).

Clemmons et al., "Insulin-like growth factor binding proteins: Mechanisms of action at the cellular level" *Modern Concepts of Insulin-like Growth Factors*, E. M. Spencer, New York, N.Y.:Elsevier pp. 475-486 (1991).

Clemmons, D., "Insulin-like growth factor binding proteins and their role in controlling IGF actions" *Cytokine & Growth Factor Reviews* 8(1):45-62 (Mar. 1997).

Conover, C., "Insulin-like growth factor binding protein proteolysis in bone cell models" *Progress in Growth Factor Research* 6(2-4):301-309 (1995).

Cooke et al., "Solution Structure of Human Insulin-Like Growth Factor 1: A Nuclear Magnetic Resonance and Restrained Molecular Dynamics Study" *Biochemistry* 30:5484-5491 (1991).

Dennis et al., "Selection and Characterization of a New Class of Peptide Exosite Inhibitors of Coagulation Factor VIIa." *Biochemistry* 40:9513-9521 (2001).

DeWolf et al., "Solution structure of a mini IGF-1" *Protein Science* 5(11):2193-2202 (Nov. 1996).

Firth, S. M. et al., "Structural Determinants of Ligand and Cell Surface Binding of Insulin-like Growth Factor-binding Protein-3" *Journal of Biological Chemistry* 273(5):2631-2638 (Jan. 30, 1998).

Fowler et al., "Insulin-like growth factor binding protein-3 (IGFBP-3) potentiates paclitaxel-induced apoptosis in human breast cancer cells" *Int. J. Cancer* 88:448-453 (2000).

Galanis et al., "Ligand-binding characteristics of recombinant amino- and carboxyl-terminal fragments of human insulin-like growth factor-binding protein-3" *Journal of Endocrinology* 169:123-133 (2001).

Garrett et al., "Crystal Structure of the First Three Domains of the Type-1 Insulin-Like Growth Factor Receptor." *Nature.* 394(6691):395-399 (Jul. 23, 1998).

Gill et al., "Insulin-like Growth Factor-binding Protein (IGFBP-3) Predisposes Breast Cancer Cells to Programmed Cell Death in a Non-IGF-dependent Manner" *Journal of Biological Chemistry* 272:25602-25607 (1997).

Harris, T.J.R., "Expression of Eukaryotic Genes in *E. coli*" *Genetic Engineering*, R. Williamson, 4th edition pp. 127-185 (1983).

Heding et al., "Biosensor measurement of the binding of insulin-like growth factors I and II and their analogues to the insulin-like growth factor-binding protein-3" *Journal of Biological Chemistry* 271(24):13948-13952 (Jun. 14, 1996).

Hua et al., "Native and non-native structure in a protein-folding intermediate: spectroscopic studies of partially reduced IGF-I and an engineered alanine model" *Journal of Molecular Biology* 259(2):297-313 (Jun. 7, 1996).

Jansson et al., "Structural Changes in Insulin-Like Growth Factor (IGF) I Mutant Proteins Affecting Binding Kinetic Rates to IGF Binding Protein 1 and IGF-I Receptor" *Biochemistry* 36:4108-4117 (1997).

Jansson et al., "The Insulin-Like Growth Factor (IGF) Binding Protein 1 Binding Epitope on IGF-I Probed by Heteronuclear NMR Spectroscopy and Mutational Analysis." *J. Biol. Chem.* 273(38):24701-24707 (Sep. 18, 1998).

Jones and Clemmons., "Insulin-Like Growth Factors and Their Binding Proteins: Biological Actions." *Endocrine Rev.* 16(1):3-34 (1995).

Kalus et al., "Structure of the IGF-binding domain of the insulin-like growth factor-binding protein-5 (IGFBP-5): implications for IGF and IGF-I receptor interactions" *EMBO Journal* 17(22):6558-6572 (Nov. 16, 1998).

Laajoki et al., "Solution Structure and Backbone Dynamics of Long- [$Arg^3$] Insulin-Like Growth Factor-I." *J. Bio. Chem.* 275(14):10009-10015 (2000).

Lalou et al., "A proteolytic fragment of insulin-like growth factor (IGF) binding protein-3 that fails to bind IGFs inhibits the mitogenic effects of IGF- I and insulin" *Endocrinology* 137:3206-3212 (1996).

LaTour et al., "Inhibitory insulin-like growth factor-binding protein: cloning, complete sequence, and physiological regulation" *Mol. Endocrinol.* 4:1806-1814 (1990).

Lee et al., "Insulin-Like Growth Factor (IGF) Binding Protein Complementary Deoxyribonucleic Acid from Human HEP G2 Hepatoma Cells: Predicted Protein Sequence Suggests an IGF Binding Domain Different from Those of the IGF-I and IGF-II Receptors" *Mol. Endocrinol.* 2(5):404-411 (1988).

Leung et al., "Growth hormone receptor and serum binding protein: purification, cloning and expression" *Nature* 330:537-543 (1987).

Liu et al., "Direct Functional Interactions between Insulin-like Growth Factor-binding Protein-3 and Retinoid X Receptor- Regulate Transcriptional Signaling and Apoptosis" *Journal of Biological Chemistry* 275:33607-33613 (2000).

Ljungquist et al., "Immobilization and affinity purification of recombinant proteins using histidine peptide fusions" *European Journal of Biochemistry* 186:563-569 (1989).

Ljungquist et al., "Thiol-directed immobilization of recombinant IgG-binding receptors" *European Journal of Biochemistry* 186:557-561(1989).

Loddick et al., "Displacement of insulin-like growth factors from their binding proteins as a potential treatment for stroke" *Proc. Natl. Acad. Sci. USA* 95(4):1894-1898 (Feb. 17, 1998).

Lowman et al., "Molecular Mimics of Insulin-Like Growth Factor 1 (IGF-1) for Inhibiting IGF-1: IGF-Binding Protein Interactions." *Biochemistry* 37(25):8870-8878 (1998).

Maile et al., "The Role of Cell Surface Attachment and Proteolysis in the Insulin-Like Growth Factor (IGF) -Independent Effects of IGF-Binding Protein-3 on Apoptosis in Breast Epithelial Cells" *Endocrinology* 140:4040-4045 (1999).

Marston, "The purification of eukaryotic polypeptides synthesized in *Escherichia coli*" *Biochemical Journal* 240:1-12 (1986).

Martin & Baxter, "Insulin-like Growth Factor-binding Protein from Human Plasma. Purification and Characterization" *Journal of Biological Chemistry* 261(19):8754-8760 (1986).

Martin and Baxter, "Regulation and actions of the insulin-like growth factor binding proteins" *Current Opinion in Endocrinology and Diabetes* pp. 16-21 (1994).

McCaig et al., "Differential interactions between IGFBP-3 and transforming growth factor-beta (TGF-$\beta$) in normal vs cancerous breast epithelial cells" *Br. J. Cancer* 86:1963-1969 (2002).

McInnes and Sykes, "Growth factor receptors: structure, mechanism, and drug discovery" *Biopolymers* 43(5):339-366 (1998).

Mohan et al., "Isolation of an inhibitory insulin-like growth factor (IGF) binding protein from bone cell-conditioned medium: A potential local regulator of IGF action" *Proc. Natl. Acad. Sci.* 86:8338-8342 (1989).

Nilsson et al., "A synthetic IgG-binding domain based on staphylococcal protein A" *Protein Eng.* 1:107-113 (1987).

Oh et al., "Characterization of the Affinities of Insulin-Like Growth Factor (IGF)-Binding Proteins 1-4 for IGF-I, IGF-II, IGF-I/Insulin Hybrid, and IGF-I Analogs." *Endocrinology.* 132:1337-1344 (1993).

Perks et al., "A non-IGF binding mutant of OGFBP-3 modulates cel function in breast epithelial cells" *Biochim. Biophys. Res. Comm.* 294:988-994 (2002).

Peterkofsky et al., "Elevated Activity of Low Molecular Weight Insulin-Like Growth Factor-Binding Proteins in Sera of Vitamin C-Deficient and Fasted Guinea Pigs" *Endocrinology* 128(4):1769-1779 (1991).

Pietrzkowski et al., "Inhibition of Cellular Proliferation by Peptide Analogues of Insulin-Like Growth Factor 1." *Cancer Research.* 52:6447-6451 (1992).

Salahifar et al., "Characterization of an amino-terminal fragment of insulin-like growth factor binding protein-3 and its effects in MCF-7 breast cancer cells" *Growth Hormone & IGF Research* 10:367-377 (2000).

Samuelsson et al., "Facilitated In Vitro Refolding of Human Recombinant Insulin-Like Growth Factor I Using a Solubilizing Fusion Partner" *Bio/Technology* 9:363-366 (1991).

Sato et al., "Three-Dimensional Structure of Human Insulin-Like Growth Factor-I (IGF-I) Determined by $^1$H-NMR and Distance Geometry." *Int. J. Pep. Protein Res.* 41:433-440 (1993).

Schmid et al., "Intact but not truncated insulin-like growth factor binding protein-3 (IGFBP-3) blocks IGF I-induced stimulation of osteoblasts: Control of IGF signalling to bone cells by IGFBP-3-specific proteolysis?" *Biochem. Biophys. Res Com.* 179:579-585 (1991).

Shimasaki et al., "Identification of Five Different Insulin-like Growth Factor Binding Proteins (IGFBPs) from Adult Rat Serum and Molecular Cloning of a Novel IGFBP-5 in Rat and Human" *The Journal of Biological Chemistry* 266:10646-10653 (1991).

Shimasaki et al., "Isolation and molecular characterization of three novel insulin-like growth factor binding proteins (IGFBP-4, 5 and 6)" *Modern Concepts of Insulin-Like Growth Factors*, E. Martin Spencer, New York:Elsevier pp. 343-358 (1991).

Shimasaki et al., "Molecular cloning of the cDNAs encoding a novel insulin-like growth factor-binding protein from rat and human" *Molecular Endocrinology* 4:1451-1458 (1990).

Sliecker et al., "Insulin and IGF-I analogs: Novel approaches to improved insulin pharmacokinetics" *Adv. Experimental Med. Biol.* 343:25-32 (1994).

Terasawa et al., "Solution structure of human insulin-like growth factor II; recognition sites for receptors and binding proteins" *EMBO Journal* 13(23):5590-5597 (Dec. 1, 1994).

Torres et al., "Solution Structure of Human Insulin-Like Growth Factor II: Relationship to Receptor and Binding Protein Interactions." *J. Mol. Bio.* 248(2):385-401 (Apr. 28, 1995).

Ullrich et al., "Insulin-like growth factor I receptor primary structure: comparison with insulin receptor suggests structural determinants that define functional specificity" *EMBO Journal* 5(10):2503-2512 (1986).

Vorwerk et al., "Binding Properties of Insulin-Like Growth Factor Binding Protein-3 (IGFBP-3), IGFBP-3 N- and C-Terminal Fragments, and Structurally Related Proteins mac25 and Connective Tissue Growth Factor Measured Using a Biosensor" *Endocrinology* 143:1677-1685 (2002).

Weinzimer et al., "Transferrin Is an Insulin-Like Growth Factor-Binding Protein-3 Binding Protein" *J. Clin. Endocrinol. Metab.* 86:1806-1813 (2001).

Wood et al., "Cloning and expression of the growth hormone-dependent insulin-like growth factor-binding protein" *Molecular Endocrinology* 2:1176-1185 (1988).

Yamanaka et al., "Characterization of Insulin-Like Growth Factor Binding Protein-3 (IGFBP-3) Binding to Human Breast Cancer Cells: Kinetics of IGFBP-3 Binding and Identification of Receptor Binding Domain on the IGFBP-3 Molecule" *Endocrinology* 140:1319-1328 (1999).

Yee et al., "Insulin-Like Growth Factor Binding Protein 1 Expression Inhibits Insulin-Like Growth Factor I Action in MCF-7 Breast Cancer Cells." *Cell Growth & Diff.* 5:73-77 (1994).

Zapf et al., "Isolation from Adult Human Serum of Four Insulin-like Growth Factor (IGF) Binding Proteins and Molecular Cloning of One of Them That is Increased by IGF I Administration and in Extrapancreatic Tumor Hypoglycemia" *Journal of Biological Chemistry* 265:14892-14898 (1990).

Zola, H., "Using Monoclonal Antibodies: Soluble Antigens" *Monoclonal Antibodies: A Manual of Techniques*, CRC Press, Chapter 6, pp. 147-158 (1987).

* cited by examiner

IGF BINDING PROTEINS

RELATED APPLICATIONS

This is a divisional application of non-provisional application Ser. No. 10/936,059, filed on Sep. 8, 2004, now U.S. Pat. No. 7,192,738, issued Mar. 20, 2007, claiming priority under 35 USC 119(e) to provisional application No. 60/508,345 filed Oct. 3, 2003, the contents of which are incorporated herein by reference.

BACKGROUND OF THE INVENTION

1. Field of Invention

This invention relates to molecules useful in determining minimal functional regions of IGFBP-3 and for antagonizing an IGF-I or IGF-II activity.

2. Description of Background and Related Art

The insulin-like growth factors I and II (IGF-I and IGF-II, respectively) mediate multiple effects in vivo, including cell proliferation, cell differentiation, inhibition of cell death, and insulin-like activity (reviewed in Clark and Robinson, *Cytokine Growth Factor Rev.*, 7: 65-80 (1996); Jones and Clemmons, *Endocr. Rev.*, 16: 3-34 (1995)). Most of these mitogenic and metabolic responses are initiated by activation of the IGF-I receptor, an $\alpha_2\beta_2$-heterotetramer closely related to the insulin receptor (McInnes and Sykes, *Biopoly.*, 43: 339-366 (1998); Ullrich et al., *EMBO J.*, 5: 2503-2512 (1986)). The IGF-I and insulin receptors bind their specific ligands with nanomolar affinity. IGF-I and insulin can cross-react with their respective non-cognate receptors, albeit at a 100-1000-fold lower affinity (Jones and Clemmons, supra). The crystal structure describing part of the extracellular portion of the IGF-I receptor has been reported (Garrett et al., *Nature*, 394: 395-399 (1998)).

Unlike insulin, the activity and half-life of IGF-I are modulated by six IGF-I binding proteins (IGFBPs 1-6), and perhaps additionally by a more distantly related class of proteins (Jones and Clemmons, supra; Baxter et al., *Endocrinology*, 139: 4036 (1998)). IGFBPs can either inhibit or potentiate IGF activity, depending on whether they are soluble or cell-membrane associated (Bach and Rechler, *Diabetes Reviews*, 3: 38-61 (1995)). The IGFBPs bind IGF-I and IGF-II with varying affinities and specificities (Jones and Clemmons, supra; Bach and Rechler, supra). For example, IGFBP-3 binds IGF-I and IGF-II with a similar affinity, whereas IGFBP-2 and IGFBP-6 bind IGF-II with a much higher affinity than they bind IGF-I (Bach and Rechler, supra; Oh et al., *Endocrinology*, 132: 1337-1344 (1993)). WO 01/75064 discloses additional human secreted IGFBP-like polypeptides that are encoded by nucleic acid sequences isolated from cDNA libraries from adrenal gland mRNA and thymus mRNA.

Structurally, IGF-I is a single-chain, 70-amino-acid protein with high homology to proinsulin. Unlike the other members of the insulin superfamily, the C region of IGF's is not proteolytically removed after translation. The solution NMR structures of IGF-I (Cooke et al., *Biochemistry*, 30: 5484-5491 (1991); Hua et al., *J. Mol. Biol.*, 259: 297-313 (1996)), mini-IGF-I (an engineered variant lacking the C-chain; DeWolf et al., *Protein Science* 5: 2193-2202 (1996)), and IGF-II (Terasawa et al., *EMBO J.*, 13: 5590-5597 (1994); Torres et al., *J. Mol. Biol.*, 248: 385-401 (1995)) have been reported. It is generally accepted that distinct epitopes on IGF-I are used to bind receptor and binding proteins. It has been demonstrated in animal models that receptor-inactive IGF mutants are able to displace endogenous IGF-I from binding proteins and thereby generate a net IGF-I effect in vivo (Loddick et al., *Proc. Natl. Acad. Sci. USA*, 95: 1894-1898 (1998); Lowman et al., *Biochemistry*, 37: 8870-8878 (1998); U.S. Pat. Nos. 6,121,416 and 6,251,865). While residues Y24, Y29, Y31, and Y60 are implicated in receptor binding, IGF mutants thereof still bind to IGFBPs (Bayne et al., *J. Biol. Chem.* 265: 15648-15652 (1990); Bayne et al., *J. Biol. Chem.*, 264: 11004-11008 (1989); Cascieri et al., *Biochemistry*, 27: 3229-3233 (1988); Lowman et al., supra).

Additionally, a variant designated (1-27, gly$^4$,38-70)-hIGF-I, wherein residues 28-37 of the C region of human IGF-I are replaced by a four-residue glycine bridge, has been discovered that binds to IGFPB's but not to IGF receptors (Bar et al., *Endocrinology*, 127: 3243-3245 (1990)).

A multitude of mutagenesis studies have addressed the characterization of the IGFBP-binding epitope on IGF-I (Bagley et al., *Biochem. J.*, 259: 665-671 (1989); Baxter et al., *J. Biol. Chem.*, 267: 60-65 (1992); Bayne et al., *J. Biol. Chem.*, 263: 6233-6239 (1988); Clemmons et al., *J. Biol. Chem.*, 265: 12210-12216 (1990); Clemmons et al., *Endocrinology*, 131: 890-895 (1992); Oh et al., supra). In summary, the N-terminal residues 3 and 4 and the helical region comprising residues 8-17 were found to be important for binding to the IGFBPs. Additionally, an epitope involving residues 49-51 in binding to IGFBP-1, -2 and -5 has been identified (Clemmons et al., *Endocrinology*, supra, 1992). Furthermore, a naturally occurring truncated form of IGF-I lacking the first three N-terminal amino acids (called des (1-3)-IGF-I) was demonstrated to bind IGFBP-3 with 25 times lower affinity (Heding et al., *J. Biol. Chem.*, 271: 13948-13952 (1996); U.S. Pat. Nos. 5,077,276; 5,164,370; and 5,470,828).

In an attempt to characterize the binding contributions of exposed amino acid residues in the N-terminal helix, several alanine mutants of IGF-I were constructed (Jansson et al., *Biochemistry*, 36: 4108-4117 (1997)). However, the circular dichroism spectra of these mutant proteins showed structural changes compared to wild-type IGF-I, making it difficult to clearly assign IGFBP-binding contributions to the mutated side chains. A different approach was taken in a very recent study where the IGFBP-1 binding epitope on IGF-I was probed by heteronuclear NMR spectroscopy (Jansson et al., *J. Biol. Chem.*, 273: 24701-24707 (1998)). The authors additionally identified residues R36, R37 and R50 to be functionally involved in binding to IGFBP-1.

Other IGF-I variants have been disclosed. For example, in the patent literature, WO 96/33216 describes a truncated variant having residues 1-69 of authentic IGF-I. EP 742,228 discloses two-chain IGF-I superagonists that are derivatives of the naturally occurring single-chain IGF-I having an abbreviated C domain. The IGF-I analogs are of the formula: BC$^n$, A wherein B is the B domain of IGF-I or a functional analog thereof, C is the C domain of IGF-I or a functional analog thereof, n is the number of amino acids in the C domain and is from about 6 to about 12, and A is the A domain of IGF-I or a functional analog thereof.

Additionally, Cascieri et al., *Biochemistry*, 27: 3229-3233 (1988) discloses four mutants of IGF-I, three of which have reduced affinity to the Type 1 IGF receptor. These mutants are: (Phe$^{23}$, Phe$^{24}$, Tyr$^{25}$) IGF-I (which is equipotent to human IGF-I in its affinity to the Types 1 and 2 IGF and insulin receptors), (Leu$^{24}$) IGF-I and (Ser$^{24}$) IGF-I (which have a lower affinity than IGF-I to the human placental Type 1 IGF receptor, the placental insulin receptor, and the Type 1 IGF receptor of rat and mouse cells), and desoctapeptide (Leu$^{24}$) IGF-I (in which the loss of aromaticity at position 24 is combined with the deletion of the carboxyl-terminal D region of hIGF-I, which has lower affinity than (Leu$^{24}$)IGF-I for the Type 1 receptor and higher affinity for the insulin receptor). These four mutants have normal affinities for human serum binding proteins.

Bayne et al., *J. Biol. Chem.* 264: 11004-11008 (1988) discloses three structural analogs of IGF-I: (1-62) IGF-I, which lacks the carboxyl-terminal 8-amino-acid D region of IGF-I; (1-27,Gly$^4$,38-70) IGF-I, in which residues 28-37 of the C region of IGF-I are replaced by a four-residue glycine bridge; and (1-27,Gly$^4$,38-62) IGF-I, with a C region glycine replacement and a D region deletion. Peterkofsky et al., *Endocrinology*, 128: 1769-1779 (1991) discloses data using the Gly$^4$ mutant of Bayne et al., supra, Vol. 264. U.S. Pat. No. 5,714,460 refers to using IGF-I or a compound that increases the active concentration of IGF-I to treat neural damage.

Cascieri et al., *J. Biol. Chem.* 264: 2199-2202 (1989) discloses three IGF-I analogs in which specific residues in the A region of IGF-I are replaced with the corresponding residues in the A chain of insulin. The analogs are: (Ile$^{41}$, Glu$^{45}$,Gln$^{46}$,Thr$^{49}$,Ser$^{50}$,Ile$^{51}$,Ser$^{53}$,Tyr$^{55}$,Gln$^{56}$) IGF-I, an A chain mutant in which residue 41 is changed from threonine to isoleucine and residues 42-56 of the A region are replaced; (Thr$^{49}$,Ser$^{50}$,Ile$^{51}$) IGF-I; and (Tyr$^{55}$,Gln$^{56}$) IGF-I.

Sliecker et al., *Adv. Experimental Med. Biol.*, 343: 25-32 (1994)) describes the binding affinity of various IGF and insulin variants to IGFBPs, IGF receptor, and insulin receptor.

IGFBPs are secreted by cells in culture and either inhibit or enhance IGF-stimulated functions (Clemmons et al., (1991) In *Modern Concepts of Insulin-like Growth Factors*. E. M. Spencer, editor. Elsevier, New York, N.Y. 475-486). Known forms of IGFBPs include IGFBP-1, having a molecular weight of approximately 30-40 kDa in humans. See, e.g., WO89/09792, published Oct. 19, 1990, pertaining to cDNA sequences and cloning vectors for IGFBP-1 and IGFBP-2; WO89/08667, published Sep. 21, 1989, relating to an amino acid sequence of IGFBP-1; and WO89/09268, published Oct. 5, 1989, relating to a cDNA sequence of IGFBP-1 and methods of expression for IGFBP-1.

IGFBP-2 has a molecular weight of approximately 33-36 kDa. See, e.g., Binkert et al., *The EMBO Journal*, 8: 2497-2502 (1989), relating to a nucleotide and deduced amino acid sequence for IGFBP-2.

IGFBP-3 has a non-glycosylated molecular weight of about 28 kDa. See, e.g., Baxter et al., *Biochim. Biophys. Res. Com.*, 139:1256-1261 (1986), pertaining to a glycosylated 53-kDa subunit of IGFBP-3 that was purified from human serum; Wood et al., *Mol. Endocrinol.*, 2:1176-1185 (1988), relating to a full-length amino acid sequence for IGFBP-3 and cellular expression of the cloned IGFBP-3 cDNA in mammalian tissue culture cells; WO 90/00569, published Jan. 25, 1990, relating to isolating from human plasma an acid-labile subunit (ALS) of IGFBP complex and the particular amino acid sequence for ALS pertaining to a subunit of IGFBP-3; and Schmid et al., *Biochim. Biophys. Res Com.*, 179: 579-585 (1991), relating to effects of full-length and truncated IGFBP-3 on two different osteoblastic cell lines.

Although initially some inconsistencies in nomenclature for IGFBP-4, IGFBP-5, and IGFBP-6 existed, in 1991 participants of the 2nd International IGF Symposium agreed upon an accepted IGFBP-4, IGFBP-5, and IGFBP-6 nomenclature. Using accepted terminology, Mohan et al., *Proc. Natl. Acad. Sci.*, 86:8338-8342 (1989) relates to an N-terminal amino acid sequence for an IGFBP-4 isolated from medium conditioned by human osteosarcoma cells, and Shimasaki et al., *Mol. Endocrinology*, 4:1451-1458 (1990) pertains to IGFBP cDNAs encoding IGFBP-4 from rat and human. WO92/03471 published Mar. 5, 1992, relates to an IGFBP-4 (originally designated therein as IGFBP-5); and WO92/03470 published Mar. 5, 1992 relates to genetic material encoding IGFBP-4 (originally designated therein as IGFBP-5).

WO92/12243 published Jul. 23, 1992, relates to IGFBP-5 (originally designated therein as IGFBP-6). Andress and Birnbaum, *Biochim. Biophys. Res Com.*, 176: 213-218 (1991) relates to the modulation of cellular action of a mixture of affinity-purified IGFBPs from U-2-cell-conditioned media on IGFs. WO92/03469 published Mar. 5, 1992, relates to genetic material encoding IGFBP-6 (originally designated therein as IGFBP-4); and WO92/03152 published Mar. 5, 1992, relates to an IGFBP-6 (originally designated therein as IGFBP-4). See also US Appln. No. 2003/0082744 as well as U.S. Pat. Nos. 6,025,465 and 5,212,074, which disclose IGFBP-6 and its fragments.

Zapf et al., *J. Biol. Chem.*, 265:14892-14898 (1990) pertains to four IGFBPs (IGFBP-2, IGFBP-3, a truncated form of IGFBP-3, and IGFBP-4) isolated from adult human serum by insulin-like growth factor (IGF) affinity chromatography and high-performance liquid chromatography. Shimasaki et al., 2nd International IGF Symposium Abstract (January 1991) discusses amino-terminal amino acids for IGFBP-4, IGFBP-5, and IGFBP-6.

When administered alone, i.e., without any IGF, the IGFBPs may also be therapeutically useful for blocking the adverse effects of IGFs, such as those that occur when IGFs are produced in excess, e.g. free IGFs secreted by certain cancer cells such as hormone-producing cancer cells such as breast or kidney cancer cells. More recently, it was demonstrated that U-2 human osteosarcoma cells secrete IGFBP-5 and IGFBP-6 (Andress and Birnbaum, supra; Shimasaki et al., *J. Biol. Chem.* 266: 10646-10653 (1991); Shimasaki et al., *Mol. Endocrinol.*, 5: 938-948 (1991)). Although affinity-purified IGF-binding proteins derived from U-2-conditioned medium clearly enhanced IGF-I stimulated mitogenesis (Andress and Birnbaum, supra), it was unclear from those studies which protein was responsible for this effect. Mohan et al. demonstrated that IGFBP-4, purified from TE-89 human osteosarcoma cells, inhibits IGF-stimulated osteoblast mitogenesis (Mohan et al., *Proc. Natl. Acad. Sci.* (U.S.A.), 86: 8338-8342 (1989); see also LaTour et al., *Mol. Endocrinol.*, 4: 1806-1814 (1990)). WO 03/068160 discloses use of IGFBP-3 for inhibiting tumor growth. WO 03/006029 discloses a method of inducing apoptosis in a cancer cell comprising increasing the expression of IGFBP-5 by the cell to an apoptosis-inducing amount. A method of killing cancer cells, a method of sensitizing cancer cells to agents that induce apoptosis, and a method of treating cancer in a patient are also described. U.S. Pat. No. 6,410,335 discloses a method of predicting risk for prostate cancer, and US Application 2001/0018190 published Aug. 30, 2001 discloses a method of treating prostate cancer with, inter alia, IGFBPs, including IGFBP-3. U.S. Pat. No. 5,840,673 and EP 871,475 disclose a method of inhibiting growth of p53-related tumors by administering IGFBP-3 or a modulator of IGFBP-3 that upregulates IGFBP-3 expression or activity. WO 00/35473 discloses use of IGFBP-6 to treat inflammatory diseases including tumor angiogenesis. WO 94/22466 discloses use of any IGFBP-3 to treat cancer, including prostate cancer. WO 92/14834 discloses two IGFBPs isolated from rat serum, one identified as IGFBP-5 useful in treating cancer.

Exploitation of the interaction between IGF and IGFBP in screening, preventing, or treating disease has been limited, however, because of a lack of specific antagonists. The application of an IGF-1/IGF-2 antagonist as a potential therapeutic adjunct in the treatment of cancer is described by Pietrzkowski et al., *Cancer Res.*, 52: 6447-6451 (1992). In that report, a peptide corresponding to the D-region of IGF-1 was synthesized for use as an IGF-1/2 antagonist. This peptide exhibited questionable inhibitory activity against IGF-1. The basis for the observed inhibition is unclear, as the D-region does not play a significant role in IGF-1 receptor (IGF-1R) binding but rather, in IGF-1 binding to the insulin receptor (Cooke et al., *Biochem.*, 30: 5484-5491 (1991); Bayne et al., *J. Biol. Chem.*, 264: 11004-11008 (1988); Yee et al., *Cell Growth and Different.* 5: 73-77 (1994)). IGF antagonists whose mechanism of action is via blockade of interactions at the IGF-1 receptor interface may also significantly alter insulin action at the insulin receptor, a disadvantage of such antagonists.

Certain IGF-1 antagonists have also been described by WO 00/23469, which discloses the portions of IGFBP and IGF peptides that account for IGF-1 and IGFBP binding, i.e., an isolated IGF binding domain of an IGFBP or modification thereof that binds IGF with at least about the same binding affinity as the full-length IGFBP. The patent publication also discloses an IGF antagonist that reduces binding of IGF to an IGF receptor, and/or binds to a binding domain of IGFBP.

Additionally, EP 639981 discloses pharmaceutical compositions comprising short peptides that function as IGF-1 receptor antagonists. The peptides used in the pharmaceutical compositions consist of less than 25 amino acids, comprise at least a portion of the C or D region from IGF-1, and inhibit IGF-1-induced autophosphorylation of IGF-1 receptors. Methods of inhibiting cell proliferation and of treating individuals suspected of suffering from or susceptible to diseases associated with undesirable cell proliferation such as cancer, restenosis, and asthma are disclosed.

Generation of specific IGF-1 antagonists has been restricted, at least in part, because of difficulties in studying the structure of IGF and IGFBP. Due to the inability to obtain crystals of IGF-1 suitable for diffraction studies, for example, an extrapolation of IGF-1 structure based on the crystal structure of porcine insulin was the most important structural road map for IGF-1 available (Blundell et al., *Proc. Natl. Acad. Sci. USA,* 75:180-184 (1978)). See also Blundell et al., *Fed Proc.*, 42: 2592 (1983), which discloses tertiary structures, receptor binding, and antigenicity of IGFs. Based on studies of chemically modified and mutated IGF-1, a number of common residues between IGF-1 and insulin have been identified as being part of the IGF-1R-insulin receptor contact site, in particular the aromatic residues at positions 23-25. Using NMR and restrained molecular dynamics, the solution structure of IGF-1 was recently reported (Cooke et al., supra). The resulting minimized structure was shown to better fit the experimental findings on modified IGF-1, as well as the extrapolations made from the structure-activity studies of insulin. Further, De Wolf et al., *Protein Sci.,* 5: 2193 (1996) discloses the solution structure of a mini-IGF-1. Sato et al., *Int. J. Pept.,* 41: 433 (1993) discloses the three-dimensional structure of IGF-1 determined by 1 H-NMR and distance geometry. Torres et al., *J. Mol. Biol.* 248: 385 (1995) discloses the solution structure of human IGF-2 and its relationship to receptor and binding protein interactions. Laajoki et al., *J. Biol. Chem.* 275: 10009 (2000) discloses the solution structure and backbone dynamics of long-(Arg(3)) IGF-1.

Peptide sequences capable of binding to insulin and/or insulin-like growth factor receptors with either agonist or antagonist activity and identified from various peptide libraries are described in WO 01/72771 published Oct. 4, 2001.

US Application No. 2003/0092631 published May 15, 2003 discloses peptides that antagonize the interaction of IGF-1 with its binding proteins, insulin receptor, and IGF receptor. These IGF antagonist peptides are useful in treating disorders involving IGF-1 as a causative agent, such as, for example, various cancers.

Regarding the structural information on the classical IGFBPs, they have a molecular mass ranging from 22 to 31 kDa and contain a total of 16-20 cysteines in their conserved amino- and carboxy-terminal domains (Bach and Rechler, supra; Clemmons, *Cytokine Growth Factor Rev.,* 8: 45-62 (1997); Martin and Baxter, *Curr. Op. Endocrinol. Diab.,* 16-21 (1994)). The central domain connecting both cysteine-rich regions is only weakly conserved and contains the cleavage sites for IGFBP-specific proteases (Chernausek et al., *J. Biol. Chem.,* 270: 11377-11382 (1995); Clemmons, supra; Conover, *Prog. Growth Factor Res.,* 6: 301-309 (1995)). Further regulation of the IGFBPs may be achieved by phosphorylation and glycosylation (Bach and Rechler supra; Clemmons, supra). There is no high-resolution structure available for any intact member of the IGFBP family. U.S. Pat. No. 6,500,635 discloses IGFBP-5 and its variants. U.S. Pat. Nos. 6,391,588 and 6,489,294 disclose truncated C-terminal IGFBP-5 fragments with reduced affinity for IGF-I as compared to full-length IGFBP-5. U.S. Pat. No. 6,369,029 discloses stimulating osteogenesis with C-terminal-truncated IGFBP-5. These compounds may be used for stimulating bone cell growth, for treating a bone disorder, or for stimulating mitogenic activity.

The NMR structures of two N-terminal fragments from IGFBP-5 that retain IGF-binding activity have recently been reported, showing that residues 40-92 of IGFBP-5 comprise the IGF binding site in the N-terminal domain of that protein (Kalus et al., *EMBO J.,* 17: 6558-6572 (1998)). Other studies have found that N-terminal fragments (residues 1-88 and 1-97) of IGFBP-3 are also able to bind IGFs (Galanis et al., *Journal of Endocrinology,* 169 (1): 123-133 (2001); Vorwerk et al., *Endocrinology,* 143 (5): 1677-1685 (2002)).

In particular, Galanis et al. have synthesized both the amino-terminal (residues 1-88; N-88) and carboxyl-terminal (residues 165-264; C-165) domains of human IGFBP-3 in bacteria, as fusion proteins with a carboxyl-terminal FLAG peptide. Although only C-165 showed binding to IGF-I and IGF-II by solution-binding assays, both N-88 and C-165 demonstrated binding to IGF-I and -II by biosensor analysis albeit with reduced affinities compared with full-length IGFBP-3. Only the carboxyl-terminal fragment (C-165) was able to form hetero-trimeric complexes with IGF-I and the acid-labile subunit (ALS).

Vorwerk et al. measured the binding of IGF-I and IGF-II to recombinant human N-terminal (residues 1-97; N-97) and C-terminal (residues 98-264; C-98) IGFBP-3 fragments and compared it with IGF binding to intact IGFBP-3 using biosensor analysis. Experiments were carried out either with binding protein or fragment immobilized or with IGF immobilized. These experiments showed that IGF-I and IGF-II bind to IGFBP-3 with affinities of $4\text{-}5\times10^{-9}$ M and similar binding kinetics. The affinities of both N-97 and C-98 for IGF proteins were approximately three orders of magnitude less than that of full-length IGFBP-3.

US Application No. 2003/0161829A1 published Aug. 28, 2003 and WO 03/025121 disclose fragments of IGFBP-3 that do not bind IGF-I to treat conditions characterized by immune stimulation rather than deficiency. The peptides target the CD74-homology domain sequence at the C-terminus of IGFBP-3 and activities localized to that region, having unique antigenicity. Peptides made to sequences in this region have previously been shown to interfere with the binding of IGFBP-3 to a number of its known ligands, including RXR-alpha, transferrin, ALS, plasminogen, fibrinogen and pre-kallikrein (Liu et al., *J. Biol. Chem.*, 275: 33607-33613 (2000); Weinzimer et al., *J. Clin. Endocrinol. Metab.*, 86: 1806-13 (2001); Campbell et al., *Am. J. Physiol.*, 275: E321-E231 (1998); Campbell et al., *J. Biol. Chem.*, 274: 30215-30221 (1999); Firth, et al., *J. Biol. Chem.*, 273: 2631-2638, (1998)).

The IGFBP-3-derived metal-binding domain peptides differ from previously disclosed IGFBP-3-derived molecules including in their inability to bind IGF-I, their unique antigenicity, and the absence of the IGFBP-3 putative death receptor (P4.33) interaction domain of IGFBP-3 (so-called "mid-region"; amino acids 88-148). The P4.33 putative death receptor is described in WO 01/87238 (Genbank Accession Number BC031217; gi:21411477). For example, WO 02/34916 teaches the use of point mutants of IGFBP-3 in which the binding to IGF-I is impaired. However, the described molecules contain the mid-region of IGFBP-3 and would be expected to exert biological effects by interacting with the P4.33 putative receptor. WO 01/87238 teaches the use of P4.33 modulators for treating disease. The metal-binding peptides do not include the P4.33 putative interaction domain (mid-region of IGFBP-3).

U.S. Pat. No. 6,417,330, WO 99/63086, and US application no. 2002/0072589 disclose IGFBP-3 variants modified to be resistant to hydrolysis. Also disclosed are variant IGFBP-3s where the nuclear localization signal (NLS) in native IGFBP-3 is altered. Additionally, amino-terminally extended IGFBP-3s are disclosed that include a variety of N-terminal extensions, including peptide and nucleotide binding domains, specific binding members such as ligand-binding domains from receptors or antigen-binding domains from immunoglobins, and peptide and protein hormones and growth factors. N-terminally extended IGFBP-3s may comprise hydrolysis-resistant or NLS-variant IGFBP-3s.

Some recent publications have described the use of IGFBP-3 peptides to treat cells in culture. The only peptides found to be active on breast cancer cells are derived from the mid-region of IGFBP-3 (McCaig et al., *Br. J. Cancer*, 86: 1963-1969 (2002); Perks et al. *Biochim. Biophys. Res. Comm.*, 294: 988-994 (2002)).

US Application No. 2003/0059430 published Mar. 27, 2003 discloses that the IGF-binding protein-derived peptides described above, including short peptides containing just 12-22 amino acids from the C-terminal domain of IGFBP-3, can mimic the full molecule's co-apoptotic, cell-penetrating, and metal-binding properties.

WO 03/052079 discloses mutants of IGFBP-3 that can inhibit DNA synthesis, can induce apoptosis, bind to neither human IGF-I nor human IGF-II, and comprise a mutation at Y57.

WO 02/098914 discloses a crystal suitable for X-ray diffraction, comprising a complex of IGF-I or -II and a polypeptide consisting of the amino acids 39-91 of IGFBP-1, the amino acids 55-107 of IGFBP-2, the amino acids 47-99 of IGFBP-3, the amino acids 39-91 of IGFBP-4, the amino acids 40-92 of IGFBP-5, or the amino acids 40-92 of IGFBP-6 or a fragment thereof consisting at least of the 9th to 12th cysteine of IGFBP-1, IGFBP-2, IGFBP-3, IGFBP-4, or IGFBP-5 or at least of the 7th to 10th cysteine of IGFBP-6; methods for the determination of the atomic coordinates of such a crystal; IGFBP mutants with enhanced binding affinity for IGF-I and/or IGF-II, and methods to identify and optimize small molecules that displace IGFs from their binding proteins.

WO 02/34916 discloses mutant IGFBP-3 polypeptides and fragments thereof that have either no binding, or diminished binding to IGFs, yet retain their ability to bind to the human IGFBP-3 receptor ("P4.33"). The fragments are N-deletion fragments with 87 to 264 amino acids. The fragment 1-87 binds poorly to IGF-I, and the other fragments (1-46, 1-75, and 1-80) do not bind at all.

WO 00/23469 discloses IGFBP fragments that account for IGF-IGFBP binding. It provides an isolated IGF binding domain of an IGFBP or modifications thereof, which binds IGF with at least about the same binding affinity as the full-length IGFBP. It also provides an IGF antagonist that reduces binding of IGF to an IGF receptor. It especially relates to IGFBP-2 fragments, but also provides the isolated IGF binding domains of IGFBP-1, IGFBP-3, IGFBP-4, IGFBP-5, and IGFBP-6. As with the IGF binding domain of IGFBP-2, the amino acid sequences comprising the IGF binding domain of the other IGFBPs could include modified forms so long as the binding affinity of the binding domain is about the same as that of the comparable native full-length IGFBP.

WO 99/32620 discloses IGFBP fragments and utilization thereof, i.e., peptides that are characterized in that the amino acid sequence parts thereof correspond to the amino acid sequence of IGFBP. The invention also relates to cyclic, glycosylated, phosphorylated, acetylated, amidated and/or sulfatized derivatives. These include C-terminal domains of IGFBP-3.

The use of gene fusions, though not essential, can facilitate the expression of heterologous peptides in *E. coli* as well as the subsequent purification of those gene products (Harris, in *Genetic Engineering*, Williamson, R., Ed. (Academic Press, London, Vol. 4, 1983), p. 127; Ljungquist et al., *Eur. J. Biochem.*, 186: 557-561 (1989); and Ljungquist et al., *Eur. J. Biochem.*, 186: 563-569 (1989)). Protein A fusions are often used because the binding of protein A, or more specifically the Z domain of protein A, to IgG provides an "affinity handle" for the purification of the fused protein. It has also been shown that many heterologous proteins are degraded when expressed directly in *E. coli*, but are stable when expressed as fusion proteins (Marston, *Biochem J.*, 240: 1 (1986)).

Fusion proteins can be cleaved using chemicals, such as cyanogen bromide, which cleaves at a methionine, or hydroxylamine, which cleaves between an Asn and Gly residue. Using standard recombinant DNA methodology, the nucleotide base pairs encoding these amino acids may be inserted just prior to the 5' end of the gene encoding the desired peptide.

Alternatively, one can employ proteolytic cleavage of fusion proteins (Carter, in *Protein Purification: From Molecular Mechanisms to Large-Scale Processes*, Ladisch et al., eds. (American Chemical Society Symposium Series No. 427, 1990), Ch 13, pages 181-193)).

There is a continuing need in the art for a molecule that can be used to elucidate binding epitopes on IGFBP-3 and other ligands, acts as an IGF antagonist to control the levels of circulating IGF as well as receptor response, for therapeutic or diagnostic uses, and can be used for other therapeutic, diagnostic, or assay purposes.

SUMMARY OF THE INVENTION

Accordingly, the invention is as claimed. In one embodiment, this invention provides a fusion protein comprising an IGFBP-3 fragment (i.e., a truncated IGFBP-3) consisting of residues 47 to 99 of native-sequence human IGFBP-3 (SEQ ID NO:1 below) linked to the synthesized Z domain of protein A from *Staphylococcus aureus*, which has the sequence:

```
VDNKFNKEQQNAFYEILHLPNLNEEQRNAFIQSLKD (SEQ ID NO:10)
DPSQSANLLAEAKKLNDAQAPK.
```

In one such embodiment, this fusion protein is displayed on phage. In another embodiment, the fragment is linked to the Z domain by means of a cleavable linker peptide. Such cleavable linker peptide preferably comprises one of the sequences: DLVD (SEQ ID NO:2), DEMD (SEQ ID NO:3), DAVD (SEQ ID NO:4), EFGGDDDK (SEQ ID NO:5), EFGGLVPRGS (SEQ ID NO:6), EFGGDLVD (SEQ ID NO:7), EFGGDEMD (SEQ ID NO:8), or EFGGDAVD (SEQ ID NO:9). In another embodiment, an ASA sequence is at the N-terminus of the Z domain. In yet another embodiment, the fragment is affinity matured.

Also provided herein is a composition comprising the fusion protein described above in a carrier, preferably a pharmaceutically acceptable carrier. Preferably, this composition is sterile.

Further provided is a nucleic acid molecule encoding the fusion protein, a vector comprising the nucleic acid, a host cell comprising the nucleic acid, and a method of producing an IGFBP-3 fusion protein comprising culturing the host cells under suitable conditions to express the fusion protein and recovering the fusion protein from the host cell culture. Preferred is that the host cells are prokaryotic, more preferably bacterial cells such as *E. coli*.

These fusion proteins can be used in many indications, including assays for determining if ligands have an IGFBP-3 binding site. The fusion proteins herein containing an IGF-I or IGF-II binding site are further useful for clarification and mapping of the IGF binding sites and binding sites of IGF-I agonist ligands other than IGF-I (e.g., peptides isolated by phage panning experiments such as bp15 described in Lowman et al., supra) on native-sequence human IGFBP-3 in the absence of any structural data.

In yet another embodiment, the invention provides a method for determining a biological activity of native-sequence human IGFBP-3, of native-sequence human IGF-I, or of native-sequence human IGF-II, or of an agonist of said IGF-I or said IGF-II in a cell-based assay comprising contacting cells with a fusion protein comprising a peptide linked to an IGFBP-3 fragment that binds to IGF-I or IGF-II, rather than with native-sequence human IGFBP-3, and determining if a biological activity attributable to native-sequence human IGFBP-3, native-sequence human IGF-I, or native-sequence human IGF-II, or an agonist of said IGF-I or said IGF-II is observed.

In one embodiment, the biological activity is apoptosis of native-sequence human IGFBP-3 that is independent of IGF-I.

In another embodiment, the assay is an IGF-dependent KIRA phosphorylation assay. This assay is a direct activity assay for the human Type 1 receptor. When a receptor in the tyrosine kinase family, such as the Type 1 IGF receptor, is activated, it is phosphorylated on tyrosine residues. In this assay cells containing the Type 1 IGF receptor are activated in vitro, then disrupted, and antibodies against the receptor are used to precipitate the IGF receptor. Next, an anti-phosphotyrosine antibody is used to assay the amount of Type 1 IGF receptor that is phosphorylated. If a fixed number of cells are used, then the amount of receptor that is phosphorylated is a direct measure of the activity of a molecule on the Type 1 IGF receptor. In this KIRA assay, cells such as a breast cancer cell line are treated with IGF-I or IGF-II plus the fusion protein and a biological activity of the fusion protein is determined by the amount of receptor that is phosphorylated.

In yet another embodiment, the biological activity is inhibition of binding of radiolabeled IGF-I or IGF-II to the cells.

In a further aspect, the invention provides a method for determining enhancement of apoptosis comprising pre-treating breast cancer cells with an IGFBP-3 fragment or fusion protein thereof that binds IGF-I or IGF-II for at least about 24 hours prior to treating the cells with an apoptotic factor, such as, for example, paclitaxel or doxorubicin, and native-sequence human IGFBP-3 or said IGFBP-3 fragment or fusion protein, and determining if the pre-treatment or treatment enhances the apoptosis induced by the treatment with the apoptotic factor, or if the amounts of pre-treatment or treatment are effective for that purpose.

DESCRIPTION OF THE PREFERRED EMBODIMENTS

A. Definitions

Figure 1:
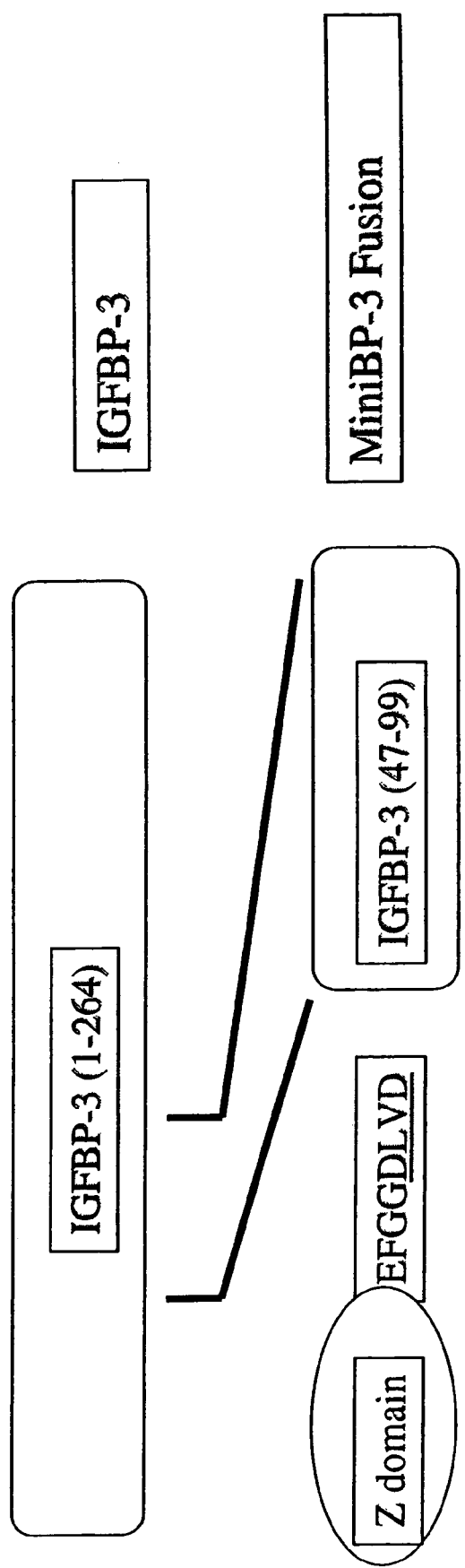
FIG. 1 shows a schematic of the miniBP-3 fusion protein. This is the fusion of a Z domain (SEQ ID NO:10) to miniBP-3 (residues 47-99 of native-sequence human IGFBP-3 (SEQ ID NO:1)) using a cleavable linker having SEQ ID NO:7 (including the caspase-3 cleavage site (SEQ ID NO:2), which is underlined).

As used herein, "IGF" refers to native insulin-like growth factor-I and native insulin-like growth factor-II as well as natural variants thereof such as brain IGF, otherwise known as des(1-3)IGF-I.

As used herein, "IGF-I" refers to insulin-like growth factor-I from any species, including bovine, ovine, porcine, equine, and human, preferably human, and from any source, whether natural, synthetic, or recombinant. This may be prepared, e.g., by the process described in EP 230,869 published Aug. 5, 1987; EP 128,733 published Dec. 19, 1984; or EP 288,451 published Oct. 26, 1988. "Native-sequence human IGF-I" or "wild-type IGF-I" is wild-type human IGF-I.

As used herein, "IGF-II" refers to insulin-like growth factor-II from any species, including bovine, ovine, porcine, equine, and human, preferably human, and from any source, whether natural, synthetic, or recombinant. It may be prepared by the method described in, e.g., EP 128,733. "Native-sequence human IGF-II" or "wild-type IGF-II" is wild-type human IGF-II.

An AIGFBP® or an "IGF binding protein" refers to a protein or polypeptide normally associated with or bound or complexed to IGF-I or IGF-II, whether or not it is circulatory (i.e., in serum or tissue). Such binding proteins do not include receptors. This definition includes IGFBP-1, IGFBP-2, IGFBP-3, IGFBP-4, IGFBP-5, IGFBP-6, Mac 25 (IGFBP-7), and prostacyclin-stimulating factor (PSF) or endothelial cell-specific molecule (ESM-1), as well as other proteins with high homology to IGFBPs. Mac 25 is described, for example, in Swisshelm et al., *Proc. Natl. Acad. Sci. USA*, 92: 4472-4476 (1995) and Oh et al., *J. Biol. Chem.*, 271: 30322-30325 (1996). PSF is described in Yamauchi et al., *Biochemical Journal*, 303: 591-598 (1994). ESM-I is described in Lassalle et al., *J. Biol. Chem.*, 271: 20458-20464 (1996). For other identified IGFBPs, see, e.g., EP 375,438 published 27 Jun. 1990; EP 369,943 published 23 May 1990; WO 89/09268 published 5 Oct. 1989; Wood et al., *Molecular Endocrinology*, 2: 1176-1185 (1988); Brinkman et al., *The EMBO J.*, 7: 2417-2423 (1988); Lee et al., *Mol. Endocrinol.*, 2: 404-411 (1988); Brewer et al., *BBRC*, 152: 1289-1297 (1988); EP 294,021 published 7 Dec. 1988; Baxter et al., *BBRC*, 147:408-415 (1987); Leung et al., *Nature*, 330: 537-543 (1987); Martin et al., *J. Biol. Chem.*, 261: 8754-8760 (1986); Baxter et al., *Comp. Biochem. Physiol.*, 91B: 229-235 (1988); WO 89/08667 published 21 Sep. 1989; WO 89/09792 published 19 Oct. 1989; Binkert et al., *EMBO J.*, 8: 2497-2502 (1989); EP 369, 943B1; U.S. Pat. No. 5,973,115; EP 1,295,939; and U.S. Pat. No. 6,004,775 and EP 546053.

"IGFBP-3" or "insulin-like growth factor binding protein-3" refers to IGFBP-3 or BP53 from any species, including bovine, ovine, porcine, equine, and human, preferably human, and from any source, whether natural, synthetic, or recombinant, as described in U.S. Pat. Nos. 5,258,287 and 5,328,891. "Native-sequence human IGFBP-3," "wild-type IGFBP-3," and "full-length IGFBP-3" is wild-type human IGFBP-3 or BP-53 as described in U.S. Pat. Nos. 5,258,287 and 5,328,891 with a glycine at position 5, i.e., SEQ ID NO:1, or an alanine at position 5, i.e., SEQ ID NO:12.

SEQ ID NO:1 is the sequence:
GASSGGLGPVVRCEPCDARALAQCAPPPAVCAELVREPGCGCCLTCALSG

QPCGIYTERCGSGLRCQPSPDEARPLQALLDGRGLCVNASAVSRLRAYLL

PAPPAPGNASESEEDRSAGSVESPSVSSTHRVSDPKFHPLHSKIIIKKG

HAKDSQRYKVDYESQSTDTQNFSSESKRETEYGPCRREMEDTLNHLKFLN

VLSPRGVHIPNCDKKGFYKKKQCRPSKGRKRGFCWCVDKYGQPLPGYTTK

GKEDVHCYSMQSK

SEQ ID NO:12 is the sequence:
GASSAGLGPVVRCEPCDARALAQCAPPPAVCAELVREPGCGCCLTCALSE

GQPCGIYTERCGSGLRCQPSPDEARPLQALLDGRGLCVNASAVSRLRAYL

LPAPPAPGNASESEEDRSAGSVESPSVSSTHRVSDPKFHPLHSKIIIKK

GHAKDSQRYKVDYESQSTDTQNFSSESKRETEYGPCRREMEDTLNHLKFL

NVLSPRGVHIPNCDKKGFYKKKQCRPSKGRKRGFCWCVDKYGQPLPGYTT

KGKEDVHCYSMQSK

"IGFBP-3 fragment" refers to native-sequence human IGFBP-3 (SEQ ID NO:1 or 12) lacking at least one amino acid. Preferably, the fragment is an N-terminal fragment such as, for example, the peptide having (or corresponding to) residues 1 to 46, residues 1 to 88, residues 1 to 89, residues 1 to 90, residues 1 to 91, residues 1 to 92, residues 1 to 93, residues 1 to 94, residues 1 to 95, residues 1 to 96, residues 1 to 97, residues 1 to 98, residues 1 to 99, residues 1 to 185, or residues 47 to 99 of native-sequence human IGFBP-3 (SEQ ID NO:1 or 12), or a C-terminal fragment such as, for example, the peptide having residues 98 to 264, residues 100 to 264, residues 165 to 264, or residues 185 to 264 of native-sequence human IGFBP-3 (SEQ ID NO:1). More preferably, the IGFBP-3 fragment is selected from the group consisting of a peptide with residues 1 to 46, residues 1 to 88, residues 1 to 97, residues 1 to 99, residues 47 to 99, residues 1 to 185, residues 98 to 264, residues 100 to 264, residues 165 to 264, and residues 185 to 264 of native-sequence human IGFBP-3 (SEQ ID NO:1 or 12), and most preferably a peptide with residues 47 to 99 of native-sequence human IGFBP-3 (SEQ ID NO:1).

A "fusion protein" is a protein having two separate peptides linked together, either directly or through a linker (i.e., "linker peptide" or "linking peptide"), preferably through such a linker. For example, one fusion protein is a protein comprising the Z domain of Protein A fused to an IGFBP-3 fragment, which Z domain and fragment may be directly linked if no cleavage is desired, or may be linked via a cleavage site such as a caspase-3 proteolytic site if cleavage is desired.

Figure 3:
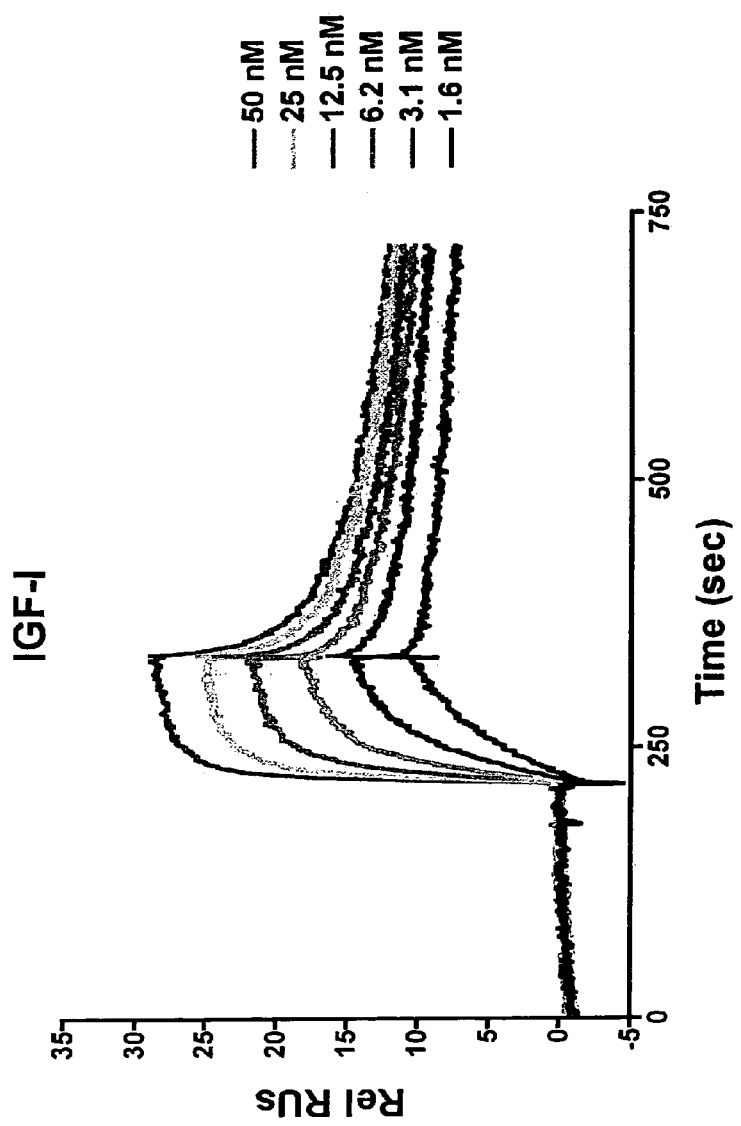
FIG. 3 shows a biosensor analysis of native-sequence human IGF-I binding to immobilized native-sequence human IGFBP-3.

As used herein, "Z domain of protein A" refers to an IgG-binding domain of *Staphylococcal* protein A as described, for example, in EP 230,869 B1 as the synthetic Z-region in FIG. 3, and in Samuelsson et al., *Bio/Technology*, 9: 363 (1991), and Nilsson et al., *Protein Eng.*, 1(2): 107-113 (1987).

"Peptides" are molecules having at least two amino acids and include polypeptides having at least about 50 amino acids. The definition includes peptide fragments, derivatives, their salts, or optical isomers, as well as linkers. Preferably, the peptides herein have from about 35 to 200 amino acids, more preferably, about 40 to 170 amino acids.

An "apoptotic factor" as used herein is a molecule that induces apoptosis or cell death. Such molecules include chemotherapeutic agents, anti-hormonal agents, cytotoxic agents and other agents some of which are defined below that induce cell death. Preferably, such factor is a chemotherapeutic agent, and more preferably doxorubicin paclitaxel, most preferably paclitaxel.

An "affinity-matured" IGFBP-3 peptide fragment or fusion protein is one having one or more alterations within the peptide fragment or fusion protein that result in an improvement in the affinity of the peptide fragment or fusion protein for IGF-I or IGF-II, compared to a corresponding parent peptide fragment or fusion protein that does not possess those alteration(s). Preferred affinity-matured IGFBP-3 peptide fragment or fusion protein will have nanomolar or even picomolar affinities for the target IGF. Affinity-matured peptide fragments and fusion proteins are produced by procedures known in the art, including phage display (Lowman and Wells, *J. Mol. Biol.,* 234 (3): 564-578 (1993); Lowman et al., *Biochemistry,* 30 (45): 10832-10838 (1991)); rational mutagenesis (Lowman et al., *J. Biol. Chem.,* 261 (17): 10982-10988 (1991); Hawkins et al., *J. Mol. Biol.,* 234 (4): 958-964 (1993)); random mutagenesis (Fiedler et al., *Protein Eng.,* 15 (11): 931-941 (2002)); and DNA shuffling and phage display (Huls et al., *Cancer Immunol. Immunother.,* 50 (3): 163-171 (2001); van den Beucken et al., *J. Mol. Biol.,* 310 (3): 591-601 (2001)).

As used herein, "mammal" for purposes of treatment refers to any animal classified as a mammal, including humans, domestic, and farm animals, and zoo, sports, or pet animals, such as dogs, horses, cats, sheep, pigs, cows, etc. The preferred mammal herein is a human. The term "non-adult" refers to mammals that are from perinatal age (such as low-birth-weight infants) up to the age of puberty, the latter being those that have not yet reached full growth potential.

As used herein, the term "treating" refers to both therapeutic treatment and prophylactic or preventative measures. Those in need of treatment include those already with the disorder as well as those prone to having the disorder or diagnosed with the disorder or those in which the disorder is to be prevented. Consecutive treatment or administration refers to treatment on at least a daily basis without interruption in treatment by one or more days. Intermittent treatment or administration, or treatment or administration in an intermittent fashion, refers to treatment that is not consecutive, but rather cyclic in nature. The treatment regime herein can be either consecutive or intermittent.

As used herein, "IGF antagonist" refers to a peptide that blocks or inhibits one or more biological activities of IGF-I or IGF-II such as its anabolic effects.

As used herein, "active" or "biologically active" IGF in the context of changing serum and tissue levels of endogenous IGF refers to IGF that binds to its receptor or otherwise causes a biological activity to occur, such as an anabolic effect.

The term "effective amount" refers to an amount of a peptide effective to treat a disease or disorder in a mammal. In the case of cancer, the effective amount of the peptide may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the peptide may prevent growth and/or kill existing cancer cells, it may be cytostatic and/or cytotoxic. For cancer therapy, efficacy in vivo can, for example, be measured by assessing the time to disease progression (TTP) and/or determining the response rates (RR).

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); hairy cell leukemia; chronic myeloblastic leukemia; and post-transplant lymphoproliferative disorder (PTLD). Preferably, the cancer comprises a tumor that expresses an IGF receptor, more preferably breast cancer, lung cancer, colorectal cancer, or prostate cancer, and most preferably breast or prostate cancer.

The term "cytotoxic agent" as used herein refers to a substance that inhibits or prevents the function of cells and/or causes destruction of cells. The term is intended to include radioactive isotopes (e.g. At211, I131, I125, Y90, Re 186, Re188, Sm153, Bi212, P32 and radioactive isotopes of Lu), chemotherapeutic agents, and toxins such as small-molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busul fan, improsulfan and piposulfan; aziridines such as benzodopa, carboquone, meturedopa, and uredopa; ethyl enimines and methylamelamines including altretamine, triethylenemel amine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, *Chem Intl. Ed. Engl.*, 33: 183-186 (1994)); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluorometlhylornithine (DMFO); retinoids such as retinoic acid; capecitabine; and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

A "growth-inhibitory agent" when used herein refers to a compound or composition that inhibits growth of a cell in vitro and/or in vivo. Thus, the growth-inhibitory agent may be one that significantly reduces the percentage of cells in S phase. Examples of growth inhibitory agents include agents that block cell cycle progression (at a place other than S phase), such as agents that induce GI arrest and M-phase arrest. Classical M-phase blockers include the vincas (vincristine and vinblastine), TAXOL® paclitaxel, and topo II inhibitors such as doxorubicin, epirubicin, daunorubicin, etoposide, and bleomycin. Those agents that arrest GI also spill over into S-phase arrest, for example, DNA alkylating agents such as tanoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antieioplastic drugs" by Murakaini et al. (W B Saunders: Philadelphia, 1995), especially p. 13.

Examples of "growth-inhibitory" anti-HER2 antibodies are those that bind to HER2 and inhibit the growth of cancer cells overexpressing HER2. Preferred growth-inhibitory anti-HER2 antibodies inhibit growth of SKBR3 breast tumor cells in cell culture by greater than 20%, and preferably greater than 50% (e.g., from about 50% to about 100%) at an antibody concentration of about 0.5 to 30 µg/ml, where the growth inhibition is determined six days after exposure of the SKBR3 cells to the antibody (see U.S. Pat. No. 5,677,171 issued Oct. 14, 1997).

An antibody that "induces cell death" is one that causes a viable cell to become nonviable. The cell is generally one that expresses the antigen to which the antibody binds, especially where the cell overexpresses the antigen. Preferably, the cell is a cancer cell, e.g., a breast, ovarian, stomach, endometrial, salivary gland, lung, kidney, colon, thyroid, pancreatic or bladder cell. In vitro, the cell may be a SKBR3, BT474, Calu 3, MDA-MB453, MDA-MB-361 or SKOV3 cell. Cell death in vitro may be determined in the absence of complement and immune effector cells to distinguish cell death induced by antibody dependent cell-mediated cytotoxicity (ADCC) or complement dependent cytotoxicity (CDC). Thus, the assay for cell death may be performed using heat-inactivated serum (i.e., in the absence of complement) and in the absence of immune effector cells. To determine whether the antibody is able to induce cell death, loss of membrane integrity as evaluated by uptake of propidium iodide (PI), trypan blue (see Moore et al. *Cytotechnology*, 17:1-11 (1995)) or 7AAD can be assessed relative to untreated cells.

An antibody that "induces apoptosis" is one that induces programmed cell death as determined by binding of annexin V, fragmentation of DNA, cell shrinkage, dilation of endoplasmic reticulum, cell fragmentation, and/or formation of membrane vesicles (called apoptotic bodies). The cell is one that expresses the antigen to which the antibody binds and may be one that overexpresses the antigen. The cell may be a tumor cell, e.g., a breast, ovarian, stomach, endometrial, salivary gland, lung, kidney, colon, thyroid, pancreatic or bladder cell. In vitro, the cell may be a SKBR3, BT474, Calu 3 cell, MDA-MB-453, MDA-MB-361 or SKOV3 cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody that induces apoptosis is one that results in about 2- to 50-fold, preferably about 5- to 50-fold, and most preferably about 10- to 50-fold, induction of annexin binding relative to untreated cell in an annexin-binding assay using cells expressing the antigen to which the antibody binds.

Examples of antibodies that induce apoptosis include the anti-HER2 monoclonal antibodies 7F3 (ATCC HB-12216), and 7C2 (ATCC HB 12215), including humanized and/or affinity-matured variants thereof; the anti-DR5 antibodies 3F1 1.39.7 (ATCC HB-12456); 3H3.14.5 (ATCC HB-12534); 3D5.1.10 (ATCC HB-12536); and 3H3. 14.5 (ATCC HB-12534), including humanized and/or affinity-matured variants thereof; the human anti-DR5 receptor antibodies 16E2 and 20E6, including affinity-matured variants thereof (WO98/51793, expressly incorporated herein by reference); and the anti-DR4 antibodies 4E7.24.3 (ATCC HB-12454); 4H6.17.8 (ATCC HB-12455); 1H5.25.9 (ATCC HB-12695); 4G7.18.8 (ATCC PTA-99); and 5GI 1.17.1 (ATCC HB-12694), including humanized and/or affinity-matured variants thereof.

In order to screen for antibodies that bind to an epitope on an antigen bound by an antibody of interest, a routine cross-blocking assay such as that described in *Antibodies, A Laboratory Manual*, eds. Harlow and Lane (New York: Cold Spring Harbor Laboratory, 1988) can be performed.

B. Modes for Carrying Out the Invention

The invention herein relates, in one aspect, to a fusion protein comprising an IGFBP-3 peptide fragment containing only residues 47-99 of native-sequence human IGFBP-3 (SEQ ID NO:1), referred to herein as miniBP-3, linked to the Z domain of Protein A, whether linked directly or through a linker, which can be cleaved by an enzyme so as to release the fragment. Such linker or linking peptide may be, for example, a cleavable linker, e.g., a caspase-3 cleavable linker containing the proteolytic site DLVD (SEQ ID NO:2), DEMD (SEQ ID NO:3) or DAVD (SEQ ID NO:4). Examples of such linking peptides are EFGGDLVD (SEQ ID NO:7), EFGGDEMD (SEQ ID NO:8), or EFGGDAVD (SEQ ID NO:9). Other examples of linking peptides are the enterokinase-cleavable linker EFGGDDDK (SEQ ID NO:5) and a thrombin-cleavable linker EFGGLVPRGS (SEQ ID NO:6).

1. Preparation

The fusion peptides of this invention can be made by chemical synthesis or by employing recombinant technology. These methods are known in the art. Chemical synthesis, especially solid phase synthesis, is preferred for short (e.g., less than 50 residues) peptides or those containing unnatural or unusual amino acids such as D-Tyr, Ornithine, amino adipic acid, and the like. Recombinant procedures are preferred for longer polypeptides. When recombinant procedures are selected, a synthetic gene may be constructed de novo or a natural gene may be mutated by, for example, cassette mutagenesis. Set forth below are exemplary general recombinant procedures.

a. Recombinant Preparation

The fusion peptide may be produced using recombinant DNA techniques. These techniques contemplate, in simplified form, taking the gene, either natural or synthetic, encoding the peptide; inserting it into an appropriate vector; inserting the vector into an appropriate host cell; culturing the host cell to cause expression of the gene; and recovering or isolating the peptide produced thereby. Preferably, the recovered peptide is then purified to a suitable degree.

Somewhat more particularly, the DNA sequence encoding an IGFBP-3 fusion protein is cloned and manipulated so that it may be expressed in a convenient host. DNA encoding parent polypeptides can be obtained from a genomic library, from cDNA derived from mRNA from cells expressing the peptide, or by synthetically constructing the DNA sequence (Sambrook et al., *Molecular Cloning: A Laboratory Manual* (2d ed.), Cold Spring Harbor Laboratory, N.Y., 1989).

The parent DNA is then inserted into an appropriate plasmid or vector that is used to transform a host cell. In general, plasmid vectors containing replication and control sequences that are derived from species compatible with the host cell are used in connection with those hosts. The vector ordinarily carries a replication site, as well as sequences that encode proteins or peptides that are capable of providing phenotypic selection in transformed cells.

For example, *E. coli* may be transformed using pBR322, a plasmid derived from an *E. coli* species (Mandel et al., *J. Mol. Biol.*, 53: 154 (1970)). Plasmid pBR322 contains genes for ampicillin and tetracycline resistance, and thus provides easy means for selection. Other vectors include different features such as different promoters, which are often important in expression. For example, plasmids pKK223-3, pDR720, and pPL-lambda represent expression vectors with the tac, trp, or $P_L$ promoters that are currently available (Pharmacia Biotechnology).

A preferred vector is pET21a. This vector is driven by the T7 promoter and is available, for example, from Novagene, Inc. and described in Studier et al., *Methods Enzymol.* 185: 60-89 (1990). Other preferred vectors are pR1T5 and pR1T2T (Pharmacia Biotechnology). These vectors contain appropriate promoters followed by the Z domain of protein A, allowing genes inserted into the vectors to be expressed as fusion proteins. Another suitable vector is pB0475, which contains origins of replication for phage and *E. coli* that allow it to be shuttled between such hosts, thereby facilitating both mutagenesis and expression (Cunningham et al., *Science*, 243: 1330-1336 (1989); U.S. Pat. No. 5,580,723).

Other preferred vectors can be constructed using standard techniques by combining the relevant traits of the vectors described above. Relevant traits include the promoter, the ribosome-binding site, the decorsin or ornatin gene or gene fusion (the Z domain of protein A and decorsin or ornatin and its linker), the antibiotic resistance markers, and the appropriate origins of replication.

The host cell may be prokaryotic or eukaryotic. Prokaryotes are preferred for cloning and expressing DNA sequences to produce the fusion protein. For example, *E. coli* K12 strain 294 (ATCC No. 31446) may be used as well as *E. coli* B, *E. coli* X1776 (ATCC No. 31537), and *E. coli* c600 and c600hfl, *E. coli* W3110 (F-, gamma-, prototrophic/ATCC No. 27325), bacilli such as *Bacillus subtilis*, and other enterobacteriaceae such as *Salmonella typhimurium* or *Serratia marcesans*, and various *Pseudomonas* species. The preferred prokaryote is *E. coli* BL21 (Stratagene), which is deficient in the OmpT and Lon proteases, which may interfere with isolation of intact recombinant proteins, and useful with T7 promoter-driven vectors, such as the pET vectors. Another suitable prokaryote is *E. coli* W3110 (ATCC No. 27325). When expressed by prokaryotes the peptides typically contain an N-terminal methionine or a formyl methionine and are not glycosylated. In the case of fusion proteins, the N-terminal methionine or formyl methionine resides on the amino terminus of the fusion protein or the signal sequence of the fusion protein. These examples are, of course, intended to be illustrative rather than limiting.

In addition to prokaryotes, eukaryotic microbes such as filamentous fungi or yeast are suitable cloning or expression hosts for fusion-protein-encoding vectors. *Saccharomyces cerevisiae* is a commonly used lower eukaryotic host microorganism. Others include *Schizosaccharomyces pombe* (Beach and Nurse, *Nature*, 290: 140 (1981); EP 139,383 published 2 May 1985); *Kluyveromyces* hosts (U.S. Pat. No. 4,943,529; Fleer et al., *Bio/Technology*, 9:968-975 (1991)) such as, e.g., *K. lactis*(MW98-8C, CBS683, CBS4574; Louvencourt et al., *J. Bacteriol.*, 154(2):737-742 (1983)), *K. fragilis* (ATCC 12,424), *K. bulgaricus* (ATCC No. 16,045), *K. wickeramii* (ATCC No. 24,178), *K. waltii* (ATCC No. 56,500), *K. drosophilarum* (ATCC No. 36,906; Van den Berg et al., *Bio/Technology*, 8:135 (1990)), *K. thermotolerans*, and *K. marxianus; yarrowia* (EP 402,226); *Pichia pastoris* (EP 183,070; Sreekrishna et al., *J. Basic Microbiol.*, 28:265-278 (1988)); *Candida; Trichoderma reesia* (EP 244, 234); *Neurospora crassa* (Case et al., *Proc. Natl. Acad. Sci. USA*, 76:5259-5263 (1979)); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.*, 112:284-289 (1983); Tilburn et al., *Gene*, 26:205-221 (1983); Yelton et al., *Proc. Natl. Acad. Sci. USA*, 81: 1470-1474 (1984)) and *A. niger* (Kelly and Hynes, *EMBO J.*, 4:475-479 (1985)). Methylotropic yeasts are suitable herein and include, but are not limited to, yeast capable of growth on methanol selected from the genera consisting of *Hansenula, Candida, Kloeckera, Pichia, Saccharomyces, Torulopsis,* and *Rhodotorula*. A list of specific species that are exemplary of this class of yeasts may be found in C. Anthony, *The Biochemistry of Methylotrophs*, 269 (1982).

Other suitable host cells for the expression of fusion proteins are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC No. CRL 1651); human embryonic kidney line (293 or 293 cells subcloned for growth in suspension culture, Graham et al., *J. Gen Virol.*, 36:59 (1977)); Chinese hamster ovary cells/-DHFR(CHO, Urlaub and Chasin, *Proc. Natl. Acad. Sci. USA*, 77:4216 (1980)); mouse sertoli cells (TM4, Mather, *Biol. Reprod.*, 23:243-251 (1980)); human lung cells (W138, ATCC No. CCL 75); human liver cells (Hep G2, HB 8065); and mouse mammary tumor (MMT 060562, ATCC No. CCL51). The selection of the appropriate host cell is deemed to be within the skill in the art.

Preferably, the Z-domain portion of the fusion protein can be secreted by the cell (has a signal sequence, for example), making it possible to isolate and purify the fusion protein from the culture medium and eliminating the necessity of destroying the host cells that arises when the desired peptide remains inside the cell. Alternatively, the fusion protein can be expressed intracellularly. It is useful to use fusion proteins that are highly expressed.

The peptide may or may not be properly folded when expressed as a fusion protein. Also, the specific peptide linker containing the cleavage site may or may not be accessible to the protease. These factors determine whether the fusion protein must be denatured and refolded, and if so, whether these procedures are employed before or after cleavage.

When denaturing and refolding are needed, typically the peptide is treated with a chaotrope, such a guanidine HCl, and is then treated with a redox buffer, containing, for example, reduced and oxidized dithiothreitol or glutathione at the appropriate ratios, pH, and temperature, such that the peptide is refolded to its native structure.

b. Synthetic Preparation

When peptides are not prepared using recombinant DNA technology, they are preferably prepared using solid-phase synthesis, such as that generally described by Merrifield, *J. Am. Chem. Soc.*, 85: 2149 (1963), although other equivalent chemical syntheses known in the art are employable. Solid-phase synthesis is initiated from the C-terminus of the peptide by coupling a protected α-amino acid to a suitable resin. Such a starting material can be prepared by attaching an amino-protected amino acid by an ester linkage to a chloromethylated resin or a hydroxymethyl resin, or by an amide bond to a BHA resin or MBHA resin. The preparation of the hydroxymethyl resin is described by Bodansky et al., *Chem. Ind*. (London), 38: 1597-1598 (1966). Chloromethylated resins are commercially available from BioRad Laboratories, Richmond, Calif. and from Lab. Systems, Inc. The preparation of such a resin is described by Stewart et al., "Solid Phase Peptide Synthesis" (Freeman & Co., San Francisco 1969), Chapter 1, pp. 1-6. BHA and MBHA resin supports are commercially available and are generally used only when the desired polypeptide being synthesized has an unsubstituted amide at the C-terminus.

The amino acids are coupled to the peptide chain using techniques well known in the art for the formation of peptide bonds. One method involves converting the amino acid to a derivative that will render the carboxyl group more susceptible to reaction with the free N-terminal amino group of the fusion protein. For example, the amino acid can be converted to a mixed anhydride by reaction of a protected amino acid with ethylchloroformate, phenyl chloroformate, sec-butyl chloroformate, isobutyl chloroformate, pivaloyl chloride or like acid chlorides. Alternatively, the amino acid can be converted to an active ester such as a 2,4,5-trichlorophenyl ester, a pentachlorophenyl ester, a pentafluorophenyl ester, a p-nitrophenyl ester, a N-hydroxysuccinimide ester, or an ester formed from 1-hydroxybenzotriazole.

Another coupling method involves use of a suitable coupling agent such as N,N'-dicyclohexylcarbodiimide or N,N'-diisopropylcarbodiimide. Other appropriate coupling agents, apparent to those skilled in the art, are disclosed in E. Gross & J. Meienhofer, *The Peptides: Analysis, Structure, Biology*, Vol. 1: Major Methods of Peptide Bond Formation (Academic Press, New York, 1979).

It should be recognized that the α-amino group of each amino acid employed in the peptide synthesis must be protected during the coupling reaction to prevent side reactions involving their active α-amino function. It should also be recognized that certain amino acids contain reactive side-chain functional groups (e.g., sulfhydryl, amino, carboxyl, and hydroxyl) and that such functional groups must also be protected with suitable protecting groups to prevent a chemical reaction from occurring at that site during both the initial and subsequent coupling steps. Suitable protecting groups, known in the art, are described in Gross and Meienhofer, *The Peptides: Analysis, Structure, Biology*, Vol. 3: "Protection of Functional Groups in Peptide Synthesis" (Academic Press, New York, 1981).

In the selection of a particular side-chain protecting group to be used in synthesizing the peptides, the following general rules are followed. An α-amino protecting group (a) must render the α-amino function inert under the conditions employed in the coupling reaction, (b) must be readily removable after the coupling reaction under conditions that will not remove side-chain protecting groups and will not alter the structure of the fusion protein, and (c) must eliminate the possibility of racemization upon activation immediately prior to coupling. A side-chain protecting group (a) must render the side-chain functional group inert under the conditions employed in the coupling reaction, (b) must be stable under the conditions employed in removing the α-amino protecting group, and (c) must be readily removable upon completion of the desired amino acid peptide under reaction conditions that will not alter the structure of the peptide chain.

It will be apparent to those skilled in the art that the protecting groups known to be useful for peptide synthesis will vary in reactivity with the agents employed for their removal. For example, certain protecting groups such as triphenylmethyl and 2-(p-biphenylyl)isopropyloxycarbonyl are very labile and can be cleaved under mild acid conditions. Other protecting groups, such as t-butyloxycarbonyl (BOC), t-amyloxycarbonyl, adamantyl-oxycarbonyl, and p-methoxybenzyloxycarbonyl, are less labile and require moderately strong acids, such as trifluoroacetic, hydrochloric, or boron trifluoride in acetic acid, for their removal. Still other protecting groups, such as benzyloxycarbonyl (CBZ or Z), halobenzyloxycarbonyl, p-nitrobenzyloxycarbonyl cycloalkyloxycarbonyl, and isopropyloxycarbonyl, are even less labile and require stronger acids, such as hydrogen fluoride, hydrogen bromide, or boron trifluoroacetate in trifluoroacetic acid, for their removal. Among the classes of useful amino-acid protecting groups are included:

(1) for an α-amino group, (a) aromatic urethane-type protecting groups, such as fluorenylmethyloxycarbonyl (FMOC) CBZ, and substituted CBZ, such as, e.g., p-chlorobenzyloxycarbonyl, p-6-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, and the like; (b) aliphatic urethane-type protecting groups, such as BOC, t-amyloxycarbonyl, isopropyloxycarbonyl, 2-(p-biphenylyl)-isopropyloxycarbonyl, allyloxycarbonyl and the like; (c) cycloalkyl urethane-type protecting groups, such as cyclopentyloxycarbonyl, adamantyloxycarbonyl, and cyclohexyloxycarbonyl; and d) allyloxycarbonyl. The preferred α-amino protecting groups are BOC or FMOC.

(2) for the side-chain amino group present in Lys, protection may be by any of the groups mentioned above in (1) such as BOC, p-chlorobenzyloxycarbonyl, etc.

(3) for the guanidino group of Arg, protection may be by nitro, tosyl, CBZ, adamantyloxycarbonyl, 2,2,5,7,8-pentamethylchroman-6-sulfonyl or 2,3,6-trimethyl-4-methoxyphenylsulfonyl, or BOC.

(4) for the hydroxyl group of Ser, Thr, or Tyr, protection may be, for example, by C1-C4 alkyl, such as t-butyl; benzyl (BZL); substituted BZL, such as p-methoxybenzyl, p-nitrobenzyl, p-chlorobenzyl, o-chlorobenzyl, and 2,6-dichlorobenzyl.

(5) for the carboxyl group of Asp or Glu, protection may be, for example, by esterification using groups such as BZL, t-butyl, cyclohexyl, cyclopentyl, and the like.

(6) for the imidazole nitrogen of His, the tosyl moiety is suitably employed.

(7) for the phenolic hydroxyl group of Tyr, a protecting group such as tetrahydropyranyl, tert-butyl, trityl, BZL, chlorobenzyl, 4-bromobenzyl, or 2,6-dichlorobenzyl is suitably employed. The preferred protecting group is 2,6-dichlorobenzyl.

(8) for the side-chain amino group of Asn or Gln, xanthyl (Xan) is preferably employed.

(9) for Met, the amino acid is preferably left unprotected.

(10) for the thio group of Cys, p-methoxybenzyl is typically employed.

An appropriately selected protecting group, in the case of Lys, BOC, protects the C-terminal amino acid, e.g., Lys, at the N-amino position. The BOC-Lys-OH can be first coupled to the benzyhydrylamine or chloromethylated resin according to the procedure set forth in Horiki et al., *Chemistry Letters* 165-168 (1978) or using isopropylcarbodiimide at about 25EC for 2 hours with stirring. Following the coupling of the BOC-protected amino acid to the resin support, the α-amino protecting group is removed, as by using trifluoroacetic acid (TFA) in methylene chloride or TFA alone. The deprotection is carried out at a temperature between about 0EC and room temperature. Other standard cleaving reagents, such as HCl in dioxane, and conditions for removal of specific α-amino protecting groups are described in the literature.

After removal of the α-amino protecting group, the remaining α-amino and side-chain protected amino acids are coupled stepwise within the desired order. As an alternative to adding each amino acid separately in the synthesis, some may be coupled to one another prior to addition to the solid-phase synthesizer. The selection of an appropriate coupling reagent is within the skill of the art. Particularly suitable as a coupling reagent is N,N'-dicyclohexyl carbodiimide or diisopropylcarbodiimide.

Each protected amino acid or amino acid sequence is introduced into the solid-phase reactor in excess, and the coupling is suitably carried out in a medium of dimethylformamide (DMF) or $CH_2Cl_2$ or mixtures thereof. If incomplete coupling occurs, the coupling procedure is repeated before removal of the N-amino protecting group prior to the coupling of the next amino acid. The success of the coupling reaction at each stage of the synthesis may be monitored. A preferred method of monitoring the synthesis is by the ninhydrin reaction, as described by Kaiser et al., *Anal. Biochem* 34: 595 (1970). The coupling reactions can be performed automatically using well-known methods, for example, a BIOSEARCH 9500™ peptide synthesizer.

Upon completion of the desired peptide sequence, the protected peptide must be cleaved from the resin support, and all protecting groups must be removed. The cleavage reaction and removal of the protecting groups is suitably accomplished simultaneously or stepwise. When the resin support is a chloromethylated polystyrene resin, the bond anchoring the peptide to the resin is an ester linkage formed between the free carboxyl group of the C-terminal residue and one of the many chloromethyl groups present on the resin matrix. It will be appreciated that reagents that are known to be capable of breaking an ester linkage and of penetrating the resin matrix can cleave the anchoring bond.

One especially convenient method is by treatment with liquid anhydrous hydrogen fluoride. This reagent not only will cleave the peptide from the resin but also will remove all protecting groups. Hence, use of this reagent will directly afford the fully deprotected peptide. When the chloromethylated resin is used, hydrogen fluoride treatment results in the formation of the free peptide acids. When the benzhydrylamine resin is used, hydrogen fluoride treatment results directly in the free peptide amines. Reaction with hydrogen fluoride in the presence of anisole and dimethylsulfide at 0° C. for one hour will simultaneously remove the side-chain protecting groups and release the peptide from the resin.

When it is desired to cleave the peptide without removing protecting groups, the protected peptide-resin can undergo methanolysis to yield the protected peptide in which the C-terminal carboxyl group is methylated. The methyl ester is then hydrolyzed under mild alkaline conditions to give the free C-terminal carboxyl group. The protecting groups on the peptide chain then are removed by treatment with a strong acid, such as liquid hydrogen fluoride. A particularly useful technique for methanolysis is that of Moore et al., *Peptides, Proc. Fifth Amer. Pept. Symp.*, M. Goodman and J. Meienhofer, Eds., (John Wiley, N.Y., 1977), p. 518-521, in which the protected peptide-resin is treated with methanol and potassium cyanide in the presence of crown ether.

Another method for cleaving the protected peptide from the resin when the chloromethylated resin is employed is by ammonolysis or by treatment with hydrazine. If desired, the resulting C-terminal amide or hydrazide can be hydrolyzed to the free C-terminal carboxyl moiety, and the protecting groups can be removed conventionally.

It will also be recognized that the protecting group present on the N-terminal α-amino group may be removed preferentially either before or after the protected peptide is cleaved from the support.

Purification of the polypeptides of the invention is typically achieved using conventional procedures such as preparative HPLC (including reversed-phase HPLC) or other known chromatographic techniques such as gel permeation, ion exchange, partition chromatography, affinity chromatography (including monoclonal antibody columns), or countercurrent distribution.

The peptides of this invention may be stabilized by polymerization. This may be accomplished by crosslinking monomer chains with polyfunctional crosslinking agents, either directly or indirectly, through multi-functional polymers. Ordinarily, two substantially identical polypeptides are crosslinked at their C- or N-termini using a bifunctional crosslinking agent. The agent is used to crosslink the terminal amino and/or carboxyl groups. Generally, both terminal carboxyl groups or both terminal amino groups are crosslinked to one another, although by selection of the appropriate crosslinking agent the alpha-amino group of one polypeptide is crosslinked to the terminal carboxyl group of the other polypeptide. Preferably, the polypeptides are substituted at their C-termini with cysteine. Under conditions well known in the art a disulfide bond can be formed between the terminal cysteines, thereby crosslinking the polypeptide chains. For example, disulfide bridges are conveniently formed by metal-catalyzed oxidation of the free cysteines or by nucleophilic substitution of a suitably modified cysteine residue. Selection of the crosslinking agent will depend upon the identities of the reactive side chains of the amino acids present in the polypeptides. For example, disulfide crosslinking would not be preferred if cysteine was present in the polypeptide at additional sites other than the C-terminus. Also within the scope hereof are peptides crosslinked with methylene bridges.

Suitable crosslinking sites on the peptides, aside from the N-terminal amino and C-terminal carboxyl groups, include epsilon-amino groups found on lysine residues, as well as amino, imino, carboxyl, sulfhydryl and hydroxyl groups located on the side chains of internal residues of the peptides or residues introduced into flanking sequences. Crosslinking through externally added crosslinking agents is suitably achieved, e.g., using any of a number of reagents familiar to those skilled in the art, for example, via carbodiimide treatment of the polypeptide. Other examples of suitable multi-functional (ordinarily bifunctional) crosslinking agents are found in the literature.

The peptides of this invention also may be conformationally stabilized by cyclization. The peptides ordinarily are cyclized by covalently bonding the NB and C-terminal domains of one peptide to the corresponding domain of another peptide of this invention so as to form cyclo-oligomers containing two or more iterated peptide sequences, each internal peptide having substantially the same sequence. Further, cyclized peptides (whether cyclo-oligomers or cyclo-monomers) are crosslinked to form 1-3 cyclic structures having from 2 to 6 peptides comprised therein. The peptides preferably are not covalently bonded through α-amino and main-chain carboxyl groups (head to tail), but rather are crosslinked through the side chains of residues located in the NB and C-terminal domains. The linking sites thus generally will be between the side chains of the residues.

Many suitable methods per se are known for preparing mono- or poly-cyclized peptides as contemplated herein. Lys/Asp cyclization has been accomplished using sodium-tert-butyloxycarbonyl (Na—Boc)-amino acids on solid-phase support with Fmoc/9-fluorenylmethyl (OFm) side-chain protection for Lys/Asp; the process is completed by piperidine treatment followed by cyclization.

Glu and Lys side chains also have been crosslinked in preparing cyclic or bicyclic peptides: the peptide is synthesized by solid-phase chemistry on a p-methylbenzhydrylamine resin. The peptide is cleaved from the resin and deprotected. The cyclic peptide is formed using diphenylphosphorylazide in diluted methylformamide. For an alternative procedure, see Schiller et al., *Peptide Protein Res.* 25: 171-177 (1985). See also U.S. Pat. No. 4,547,489

Disulfide crosslinked or cyclized peptides are generated by conventional methods. The method of Pelton et al. (*J. Med. Chem.*, 29: 2370-2375 (1986)) is suitable, except that a greater proportion of cyclo-oligomers are produced by conducting the reaction in more concentrated solutions than the dilute reaction mixture described by Pelton et al., for the production of cyclo-monomers. The same chemistry is useful for synthesis of dimers or cyclo-oligomers or cyclo-monomers. Also useful are thiomethylene bridges. Lebl and Hruby, *Tetrahedron Letters*, 25: 2067-2068 (1984). See also Cody et al., *J. Med. Chem.* 28: 583 (1985).

The desired cyclic or polymeric peptides are purified by gel filtration followed by reversed-phase high-pressure liquid chromatography or other conventional procedures. The peptides are sterile filtered and formulated into conventional pharmacologically acceptable vehicles.

The starting materials required for the processes described herein are known in the literature or can be prepared using known methods and known starting materials.

If in the peptides being created carbon atoms bonded to four nonidentical substituents are asymmetric, then the peptides may exist as diastereoisomers, enantiomers or mixtures thereof. The syntheses described above may employ racemates, enantiomers or diastereomers as starting materials or intermediates. Diastereomeric products resulting from such syntheses may be separated by chromatographic or crystallization methods. Likewise, enantiomeric product mixtures may be separated using the same techniques or by other methods known in the art. Each of the asymmetric carbon atoms, when present, may be in one of two configurations R) or S) and both are within the scope of the present invention.

In another embodiment, the fragment of the fusion protein herein may be affinity matured so that it has better affinity toward the IGF-I and/or IGF-II than the parent fragment. Such affinity maturation can be done, for example, through phage display, rational mutagenesis, random mutagenesis, or DNA shuffling and phage display, or by any such other means known in the art for effecting this change. See the references noted above in the definition section.

2. Uses

There are many advantages to using the fusion proteins for the applications disclosed herein. For example, mammalian systems can be expensive for the industrial production of wild-type IGFBP-3. On the other hand, peptide fusions are expected to be cheaper and easier to produce than wild-type IGFBP-3 using either synthetic chemical methods or highly efficient biological production systems well known to those skilled in the art.

The peptides herein may be useful in diagnostic assays, e.g., for detecting expression of IGF-I in specific cells, tissues, or serum.

For diagnostic applications, the peptide typically will be labeled with a detectable moiety. Numerous labels are available that can be generally grouped into the following categories:

(a) Radioisotopes, such as 35S, 14C, I211, 3H, and 131I, are available. The peptide can be labeled with the radioisotope using the techniques described in *Current Protocols in Immunology*, Volumes 1 and 2, Coligen et al., ed. (Wiley-Interscience: New York, 1991), for example, and radioactivity can be measured using scintillation counting.

(b) Fluorescent labels such as rare-earth chelates (europium chelates) or fluorescein and its derivatives, rhodainine and its derivatives, dansyl, Lissamine, phycoerythrin and Texas Red are available. The fluorescent labels can be conjugated to the peptide using the techniques disclosed in *Current Protocols in Immunology*, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, beta-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., "Methods for the Preparation of Enzyme-Antibody Conjugates for use in Enzyme Immunoassay," in *Methods in Enzym.* (ed J. Langone & H. Van Vunakis), 73:147-166 (Academic Press, New York, 1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB));

(ii) alkaline phosphatase (AP) with para-nitrophenyl phosphate as chromogenic substrate; and (iii) beta-D-galactosidase (beta-D-Gal) with a chromogenic substrate (e.g., p-nitrophenyl-beta-D-galactosidase) or fluorogenic substrate (4-methylumbellifuryl-beta-D-galactosidase).

Numerous other enzyme-substrate combinations are available to those skilled in the art. For a general review of these, see U.S. Pat. Nos. 4,275,149 and 4,318,980.

Sometimes, the label is indirectly conjugated with the peptide. The skilled artisan will be aware of various techniques for achieving this. For example, the peptide can be conjugated with biotin and any of the three broad categories of labels mentioned above can be conjugated with avidin, or vice versa. Biotin binds selectively to avidin and thus, the label can be conjugated with the peptide in this indirect manner. Alternatively, to achieve indirect conjugation of the label with the peptide, the peptide is conjugated with a small hapten (e.g., digoxin) and one of the different types of labels mentioned above is conjugated with an anti-hapten peptide (e.g., anti-digoxin antibody). Thus, indirect conjugation of the label with the peptide can be achieved.

In another embodiment of the invention, the peptide need not be labeled, and the presence thereof can be detected using a labeled antibody that binds to the peptide.

The peptide of the present invention may be employed in any known assay method, such as competitive binding assays, direct and indirect sandwich assays, and immunoprecipitation assays. Zola, *Monoclonal Antibodies: A Manual of Techniques*, pp. 147-158 (CRC Press, Inc. 1987).

The peptide may also be used for in vivo diagnostic assays. Generally, the peptide is labeled with a radionuclide (such as 111In, 99Tc, 14C, 131I, 125I, 3H, 32P or 35S) so that the antigen or cells expressing it can be localized using immunoscintiography.

Other uses include mapping binding epitopes of bp15 and IGFBP-3 and other IGF peptide agonists. In addition, the IGFBP-3 fragments that bind to IGF-I or IGF-II or fusion proteins comprising them can be used in cell-based assays. Certain such assays comprise contacting the cell with the fusion protein rather than with native-sequence human IGFBP-3 and determining if a biological activity attributable to native-sequence human IGFBP-3, native-sequence human IGF-I or native-sequence IGF-II, or an agonist of said IGF-I or said IGF-II is observed. In one embodiment, the biological activity is apoptosis of native-sequence human IGFBP-3 that is independent of IGF-I. In another example, the assay is an IGF-dependent KIRA phosphorylation assay. This assay is an IGF-I kinase receptor activation assay, which is a direct activity assay for the human Type 1 receptor. When a receptor in the tyrosine kinase family, such as the Type 1 IGF receptor, is activated, it is phosphorylated on tyrosine residues. In this assay cells containing the Type 1 IGF receptor are activated in vitro, then disrupted, and antibodies against the receptor are used to precipitate the IGF receptor. Next, an anti-phosphotyrosine antibody is used to assay the amount of Type 1 IGF receptor that is phosphorylated. If a fixed number of cells are used, then the amount of receptor that is phosphorylated is a direct measure of the activity of a molecule on the Type 1 IGF receptor. In this KIRA assay, cells such as a breast cancer cell line are treated with IGF-I or IGF-II plus the fusion protein and a biological activity of the fusion protein is determined by the amount of receptor that is phosphorylated. KIRA assays are described further in U.S. Pat. No. 6,251,865 using MCF-7 breast cancer cells as one embodiment, and in Chen et al., *Am. J. Physiol. Endocrinol. Metab.* 284: E1149-E1155 (2003).

In yet another embodiment, the biological activity is inhibition of binding of radiolabeled IGF-I or IGF-II to the cells.

A further example is a method comprising pre-treating breast cancer cells with an IGFBP-3 fragment or fusion protein thereof that binds to IGF-I or IGF-II for at least about 24 hours prior to treating the cells with an apoptotic factor, such as, for example, a chemotherapeutic agent, e.g., doxorubicin or paclitaxel, and native-sequence human IGFBP-3 or said IGFBP-3 fragment or fusion protein, and determining if the pre-treatment or treatment enhances the apoptosis induced by the treatment with apoptotic factor, or if the amounts of pre-treatment or treatment are effective for that purpose.

Kits are also contemplated for this invention. The kit generally comprises a container containing a composition comprising the fusion protein and instructions for its use, e.g., in an assay. A typical kit would comprise a container, preferably a vial, for the fusion protein formulation comprising the fusion protein in a buffer and instructions, such as a product insert or label, directing the user to utilize the formulation, e.g., for mapping epitopes or cell-based assays. The kit optionally includes a container, preferably a vial, for an agent to be used with the fusion protein.

The invention will be more fully understood by reference to the following examples. They should not, however, be construed as limiting the scope of the invention. All literature and patent citations mentioned herein are expressly incorporated by reference.

EXAMPLE 1

Production of IGFBP-3 and miniBP-3 Fusion Protein

Introduction:

Native-sequence human IGFBP-3 and miniBP-3 fusion protein were prepared and assessed for direct binding to native-sequence human IGF-I and IGF-II in BIAcore™ assays.

Based upon the results of experiments using the miniBP-3 fusion protein described below, it is predicted that molecules of the type claimed herein should decrease active IGF levels.

Materials and Methods:

Expression and Purification of Wild-Type IGFBP-3 and miniBP-3 Fusion and Cleaved miniBP-3

Wild-type IGFBP-3 and miniBP-3 were produced in *E. coli* using the vector pET21a (Novagene) as follows:

All routine chemical reagents were purchased from Sigma Chemical Co. (St Louis, Mo.) or Fisher Scientific (Fair Lawn, N.J.). Restriction enzymes and the T4 DNA ligase were obtained from New England Biolabs (Beverley, Mass.). Oligonucleotide synthesis reagents, DNA sequencing kits, and PCR kits were obtained from PE Biosystems (Foster City, Calif.). dNTPs, IPTG and ATP were purchased from Boehringer-Mannheim (Indianapolis, Ind.). DNA polymerase and *E. coli* strain BL21 were purchased from Stratagene (La Jolla, Calif.).

Plasmid pET21a was purchased from Novagen Inc. (Madison, Wis.). The affinity column was from Pharmacia (Piscataway, N.J.). LB medium was prepared according to the standard formula (Sambrook et al., supra). HEPES and CHAPS buffers and DTT are obtainable from the sources indicated below. Periplasmic extraction buffer consisted of 10 mM TRIS-HCl, pH 8.5 and 1 mM EDTA. TE buffer consisted of 10 mM TRIS-HCl, pH 8.0 and 1 mM EDTA.

Oligodeoxyribonucleotides were synthesized using a 394 automated DNA synthesizer from PE Biosystems. PCR and sequencing primers were purified by ethanol precipitation and dissolved in TE buffer. The Z domain was amplified by PCR of vector pA-100-Z (derived from the construct as described in Dennis et al., *Biochemistry*, 40: 9513 (2001)) using the primers: 5'-ACT AAA TAT GCT AGC GCC GTA GAC AAC AAA TTC AAC AAA G-3' (SEQ ID NO:13) and 5'-ATA TTT AGT GAA TTC CTT AGG CGC CTG AGC ATC ATT TAG-3' (SEQ ID NO: 14). The amplified Z domain was digested with NheI and EcoRI and ligated into the cloning vector pET21a (Novagen) treated with the same pair of restriction enzymes to generate pET21a-Z domain fusion. The insertion of the Z domain was confirmed by sequencing.

The coding region of miniBP-3 fusion was synthesized by PCR using the gene assembly method of Stemmer et al., *Gene*, 164: 49-53 (1995). The oligonucleotides used for gene assembly had the sequences: 5'-ACT AAA TAG AAT TCG GCG GTG ATG ATG ACG ACA AAG CCC TGA GCG AAG GTC AGC CGT GCG GTA TTT AT-3' (SEQ ID NO:15), 5'-GCT CGC CGG CTG GCA ACG CAG ACC GCT ACC GCA ACG TTC GGT ATA AAT ACC GCA CGG-3' (SEQ ID NO:16), 5'-CGT TGC CAG CCG AGC CCG GAT GAA GCC CGT CCG CTG CAG GCC CTG CTG GAT GGT CGT GGT CTG TGC-3' (SEQ ID NO:17), and 5'-TAT TTA GTA AGC TTC TAA TAG GCA CGC AGA CGG CTA ACG GCG CTG GCG TTA ACG CAC AGA CCA CGA CC-3' (SEQ ID NO:18). The assembled gene was amplified using the following oligonucleotides: 5'-ACT AAA TAG AAT TCG GCG GTG ATG-3' (SEQ ID NO:19) and 5'-TAT TTA GTA AGC TTC TAA TAG GCA CG-3' (SEQ ID NO:20).

The gene encoding full-length fusion miniBP-3 protein was amplified with the primers using a PCR System 9700™ thermocycler (PE Biosystems) as described in Cao et al., *Gene*, 197: 205-214 (1997). The amplified product was digested with Eco RI and Hind III and ligated into the pET21a-Z-domain-containing vector treated with the same pair of restriction enzymes to generate pET21a-miniBP-3 fusion. The insertion of the miniBP-3 fragment was confirmed by sequencing. The enterokinase cleavage site EFG-GDDDDK (SEQ ID NO:4) was later replaced with the caspase-3 cleavage site EFGGDLVD (SEQ ID NO:7) using the QUIKCHANGE™ Site-Directed Mutagenesis Kit. These two mutagenic primers had the sequences: 5'-GGA ATT CGG CGG TGA TCT GGT GGA TGC CCT GAG CGA AGG-3' (SEQ ID NO:21) and 5'-CCT TCG CTC AGG GCA TCC ACC AGA TCA CCG CCG AAT TCC-3' (SEQ ID NO: 22). The mutation was confirmed by sequencing.

This vector was transformed into E. coli strain BL21 (Stratagene). Inserts in pET expression vectors were sequenced in both orientations to ensure that the plasmid constructs were free of PCR or ligation errors.

The cells were propagated overnight at 37° C. in 2YT medium (Sambrook et al, supra) containing 50 μg/ml of ampicillin. Overnight cultures were diluted 100-fold into the same medium, grown until the optical density of the culture reached 0.5 at 600 nm, then induced by the addition of isopropyl-beta-D-thiogalactopyranoside (IPTG) to a final concentration of 50 μM and grown for an additional 4 hours under the same conditions. Cells were collected by centrifugation, frozen/thawed at −20/4° C. in periplasmic extraction buffer, and clarified by centrifugation as described by Cao et al., supra.

The periplasmic extracts from the centrifugation were subjected to chromatography using an IgG SEPHAROSE™ ion-exchange column (Amersham Biosciences) as described in Nilssen et al., supra. Briefly, the column was washed with 5 volumes 50 mM TRIS buffer, pH 7.6, 150 mM NaCl and 0.05% TWEEN-20™ buffer (TST), then alternately with 0.5 M acetic acid (HAc), pH 3.4 and TST for two cycles. The column was equilibrated with TST and the fusion protein was captured on the column, as described in Nilsson et al., supra. The column was washed with 10 bed volumes TST and 2 bed volumes of 5 mM ammonium acetate, pH 5.0 before elution.

Figure 2:
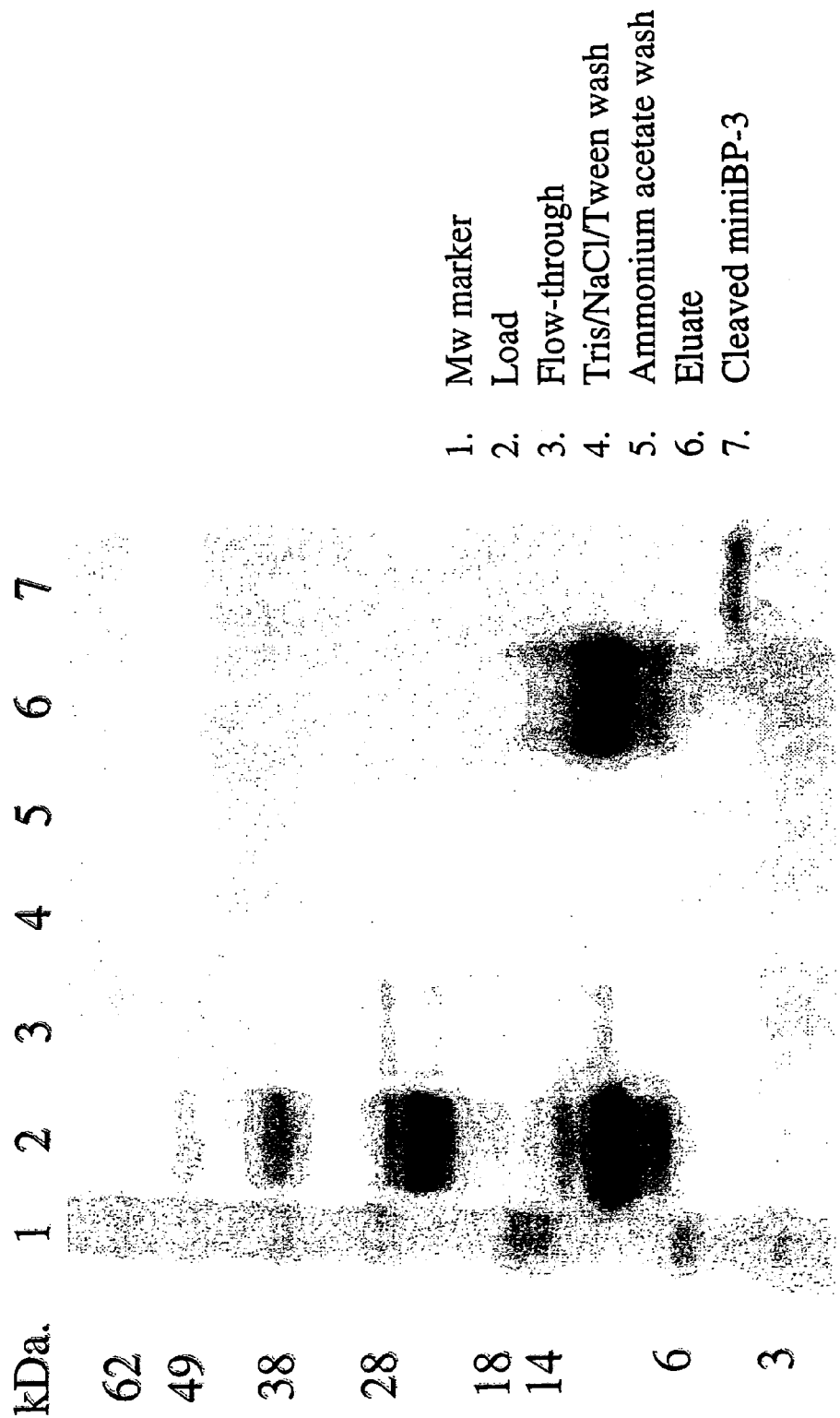
FIG. 2 shows a SDS-PAGE analysis, using Coomassie blue staining, of various chromatographic fractions of the miniBP-3 fusion protein and the cleaved protein miniBP-3.

After the fusion protein was eluted with 4 bed volumes of 0.5M HAc it was incubated overnight at 4° C. with 125 nM caspase-3 (kindly provided by Dr. Guy Salvesen, The Burnham Institute, La Jolla, Calif.) in 100 mM Hepes buffer (ProSciTech), 0.1% CHAPS lysis buffer (Chemicon International), 0.5 mM dithiothreitol (DTT) (J T Baker), pH 7.5. Cleaved miniBP-3 was recovered from the supernatant of the reaction after centrifugation. The purity of the fusion protein was verified by SDS-PAGE analysis followed by visualizing the overloaded gel with routine Coomassie brilliant blue R staining. See FIG. 2, which shows the SDS-PAGE analysis for the various stages.

BL21 cells expressing wild-type IGFBP-3 were cultured and expression was induced as with miniBP-3. The wild-type IGFBP-3 was extracted from inclusion bodies and refolded in vitro using standard conditions. Purification was achieved using ion-exchange chromatography on both Q and S SEPHAROSE™ (Amersham Biosciences) columns and hydrophobic-interaction chromatography on a phenyl SUPEROSE™ (Amersham Biosciences) column using standard techniques.

Biosensor Kinetic Measurements

The binding affinities of wild-type IGFBP-3 and miniBP-3 fusion protein for IGF-I and IGF-II were determined using a BIAcore™-2000 real time kinetic interaction analysis system (BIAcore, Inc., Piscataway, N.J.) to measure association ($k_a$) and dissociation ($k_d$) rates. Two types of chips were prepared for this purpose.

CM5 Chip Preparation:

Carboxymethylated dextran biosensor chips (CM5, BIAcore Inc.) were activated with EDC (N-ethyl-N'-(3-dimethylaminopropyl)-carbodiimide hydrochloride) and NHS(N-hydroxysuccinimide) according to the supplier's instructions. For immobilization, wild-type IGFBP-3 and mutants in 10 mM sodium acetate, pH 4, were injected onto the biosensor chip at a concentration of 0.2 mg/ml to yield approximately 450-700 RU's (resonance-response units) of covalently coupled protein. Unreacted groups were blocked with an injection of 1 M ethanolamine.

Kinetic measurements were carried out by injecting two-fold serial dilutions of IGF-I or IGF-II in PBST running buffer (PBS, 0.05% TWEEN-20™ buffer, 0.01% sodium azide) at 25° C. using a flow rate of 20 or 50:1/min. IGF concentrations ranged between 0.4 nM and 50 nM for IGFBP-3 and 100 nM to 25:M for miniBP-3 fusion. For both proteins, association and dissociation rates were calculated using a 1:1 Langmuir association model in the BIAcore™ evaluation software. For wild-type IGFBP-3, the equilibrium dissociation constant was calculated as $k_d/k_a$. For miniBP-3 fusion, the equilibrium dissociation constant was calculated by plotting equilibrium binding data in GraphPad Prism™ software (GraphPad Software Inc., San Diego, Calif.) and fitting to a one-site binding model.

SA Chip Preparation:

Streptavidin-coated chips were conditioned according to the manufacturer's instructions (BIAcore, Inc.) prior to injection of 0.02 mg/ml of biotinylated IGF-I or IGF-II in 10 mM sodium acetate pH 4. Biotinylated IGF-I and IGF-II were prepared using EZ-Link biotinylation reagents according to the manufacturer's instructions (Pierce). Between 100 and 1000 RUs were immobilized on the chip.

Kinetic measurements were carried out by injecting two-fold serial dilutions of miniBP-3 fusion protein in PBST running buffer at 50:1/min. Concentrations were between 250 nM and 32:M.

Competition binding experiments were carried out as follows. 15 nM to 100:M bp15 peptide and 20 nM IGFBP-3 were incubated for 1 hour at room temperature before injection at 20:1/min in PBST over immobilized biotinylated IGF-I and -II. Equilibrium binding data was plotted in GraphPad Prism™ software and fit to a one-site competition-binding model.

Results:

The wild-type IGFBP-3 and mini BP-3 fusion protein were submitted for kinetic analysis using a BIAcore™ instrument and tested for binding affinity to IGF-I and IGF-II. The results are shown in Table I for wild-type IGFBP-3 and Table II for miniBP-3 fusion protein.

TABLE I

Kinetic Parameters for the Interaction of Purified Wild-type IGFBP-3 with IGF-I and -II Determined by BIAcore ™ Analysis

|  | $k_a$ (×10$^4$ M$^{-1}$ s$^{-1}$) | $k_d$ (×10$^{-4}$ s$^{-1}$) | $K_D$ (×10$^{-9}$ M) |
| --- | --- | --- | --- |
| IGF-I | 715 ± 3.66 | 7.58 ± 0.07 | 0.11 ± 0.001 |
| IGF-II | 348 ± 1.02 | 4.07 ± 0.05 | 0.12 ± 0.001 |

TABLE II

Kinetic Parameters for the Interaction of Purified MiniBP-3 Fusion Protein with IGF-I and -II Determined by BIAcore ™ Analysis

|  | $k_a$ (×10$^4$ M$^{-1}$ s$^{-1}$) | $k_d$ (s$^{-1}$) | $K_D$ (×10$^{-6}$ M) |
| --- | --- | --- | --- |
| IGF-I | 9.13 ± 0.87 | 0.59 ± 0.04 | 4.64 ± 0.17 |
| IGF-II | 7.59 ± 1.35 | 0.08 ± <0.01 | 4.66 ± 0.06 |

Figure 4:
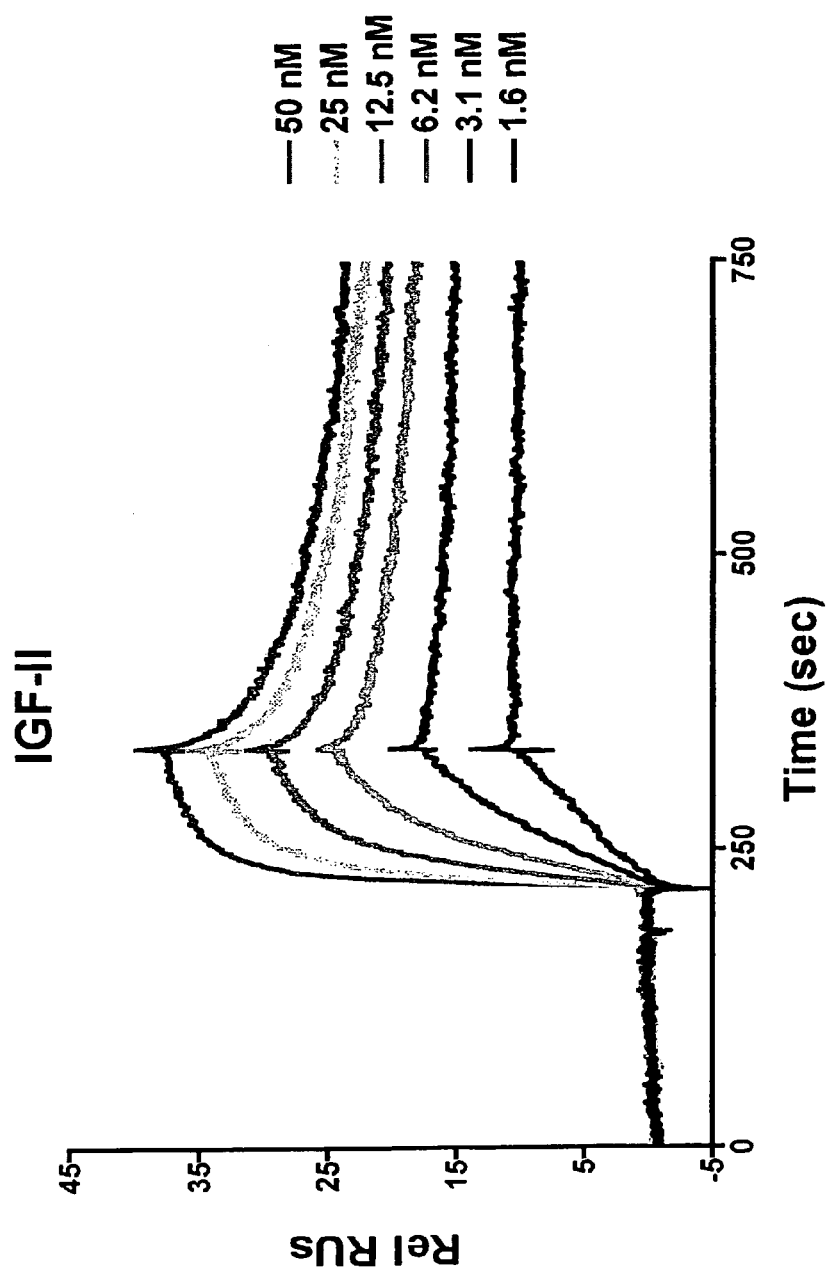
FIG. 4 shows a biosensor analysis of native-sequence human IGF-II binding to immobilized native-sequence human IGFBP-3.
Figure 5:
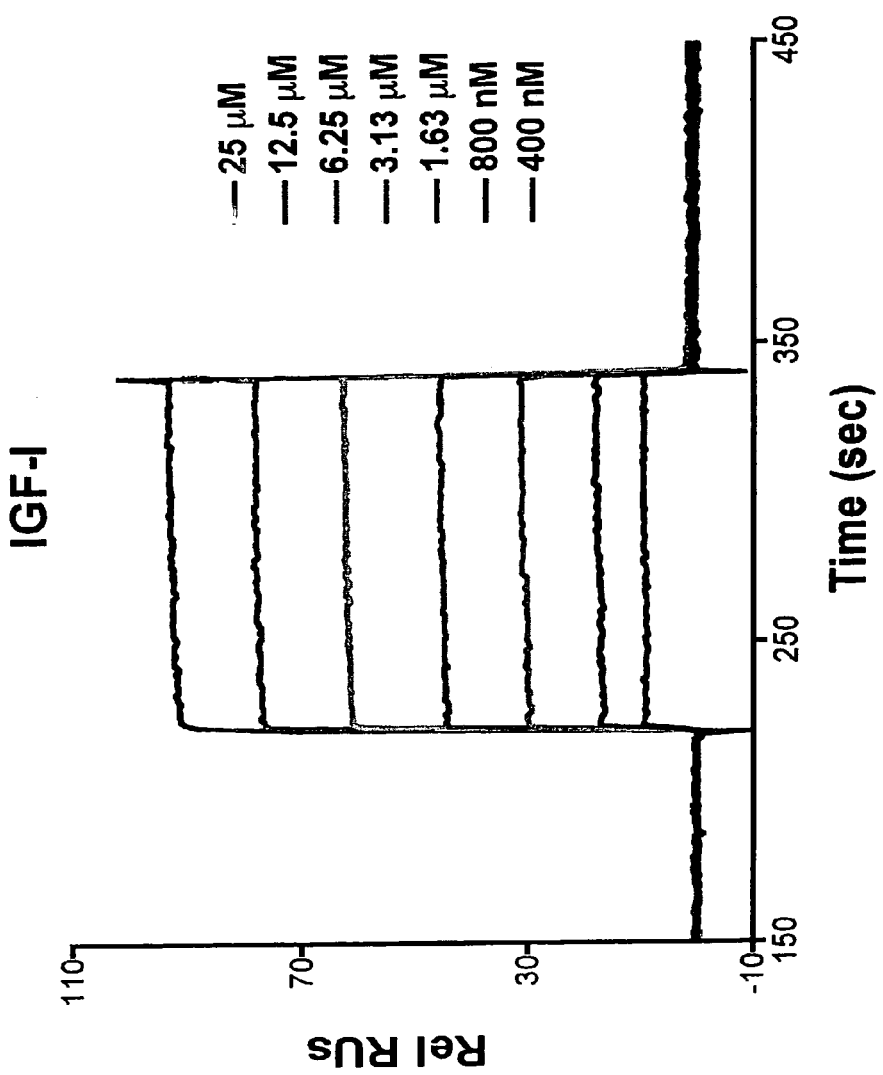
FIG. 5 shows a biosensor analysis of native-sequence human IGF-I binding to immobilized miniBP-3 fusion protein.
Figure 6:
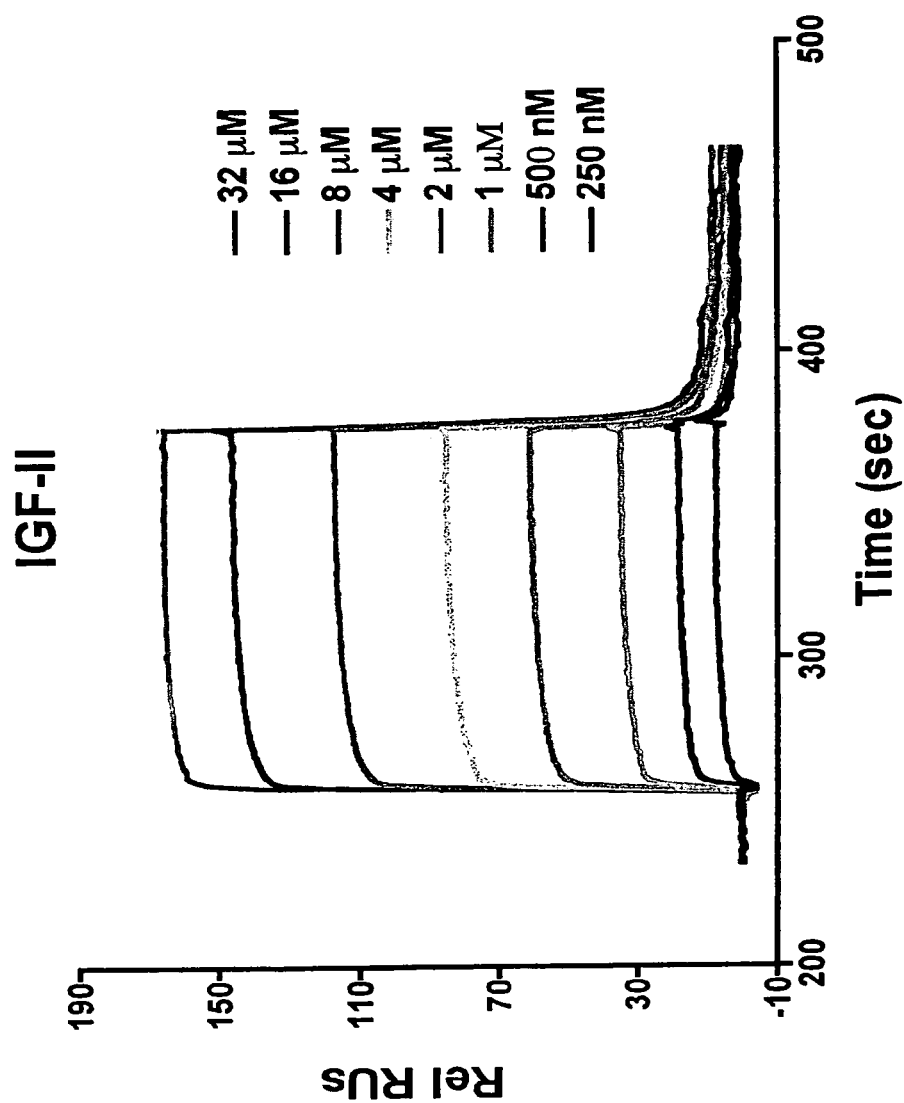
FIG. 6 shows a biosensor analysis of native-sequence human IGF-II binding to immobilized miniBP-3 fusion protein.

The results in Table I (see also FIGS. 3 and 4), showing that IGFBP-3 has high affinity for IGF-I and IGF-II, compare favorably with other measurements in the literature. The results in Table II (see also FIGS. 5 and 6) as compared to Table I show that the miniBP-3 fusion has lower affinity for IGF-I and IGF-II compared to wild-type IGFBP-3. Without being limited to any one theory, it is believed that this is primarily due to increases in off-rate. Studies with other fragments of IGFBP-3 display similar findings, as shown in Table III.

TABLE III

Kinetic Parameters for the Interaction of Purified N-Terminal Fragments of
IGFBP-3 with IGF-I and -II Determined by BIAcore ™ Analysis

| Fragment | $k_a$ ($\times 10^4$ M$^{-1}$ s$^{-1}$) | $k_d$ (s$^{-1}$) | $K_A$ ($\times 10^5$ M$^{-1}$) | Reference |
|---|---|---|---|---|
| N-88 | 14.7 ± 1.6 | 1.26 ± 0.28 × 10$^{-2}$ | 103 ± 8 | Galanis et al. (2001), supra |
| IGFBP-3$^{1-97}$ | 3.2 ± 1.1 | 5.55 ± 1.40 × 10$^{-3}$ | 61.4 ± 19.8 | Vorwerk et al. (2002), supra |

EXAMPLE 2

Binding of Peptide bp15 to MiniBP-3 Fusion

Figure 7:
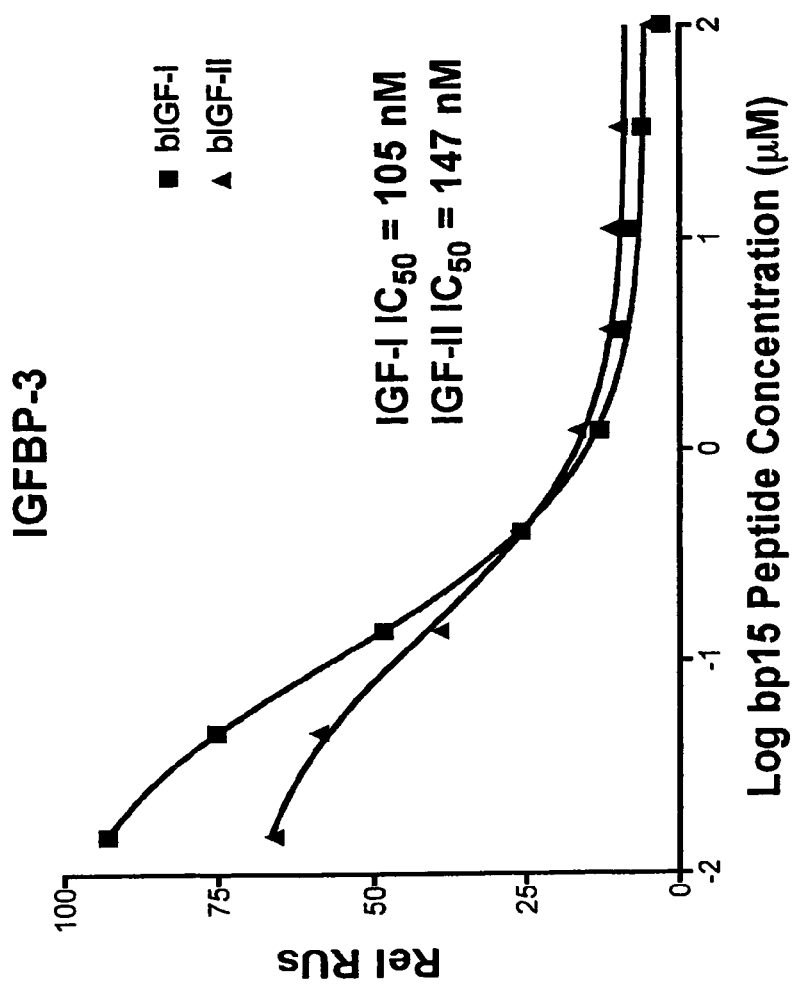
FIG. 7 shows the results of peptide bp15 (SEEVCWP-VAEWYLCN) (SEQ ID NO:11) competition experiments performed on the BIAcore™ analyzer. A total of 15 nM to 100:M bp15 peptide and 20 nM native-sequence human IGFBP-3 were incubated for 1 hour at room temperature before injection over immobilized biotinylated native-sequence human IGF-I and -II.
Figure 8:
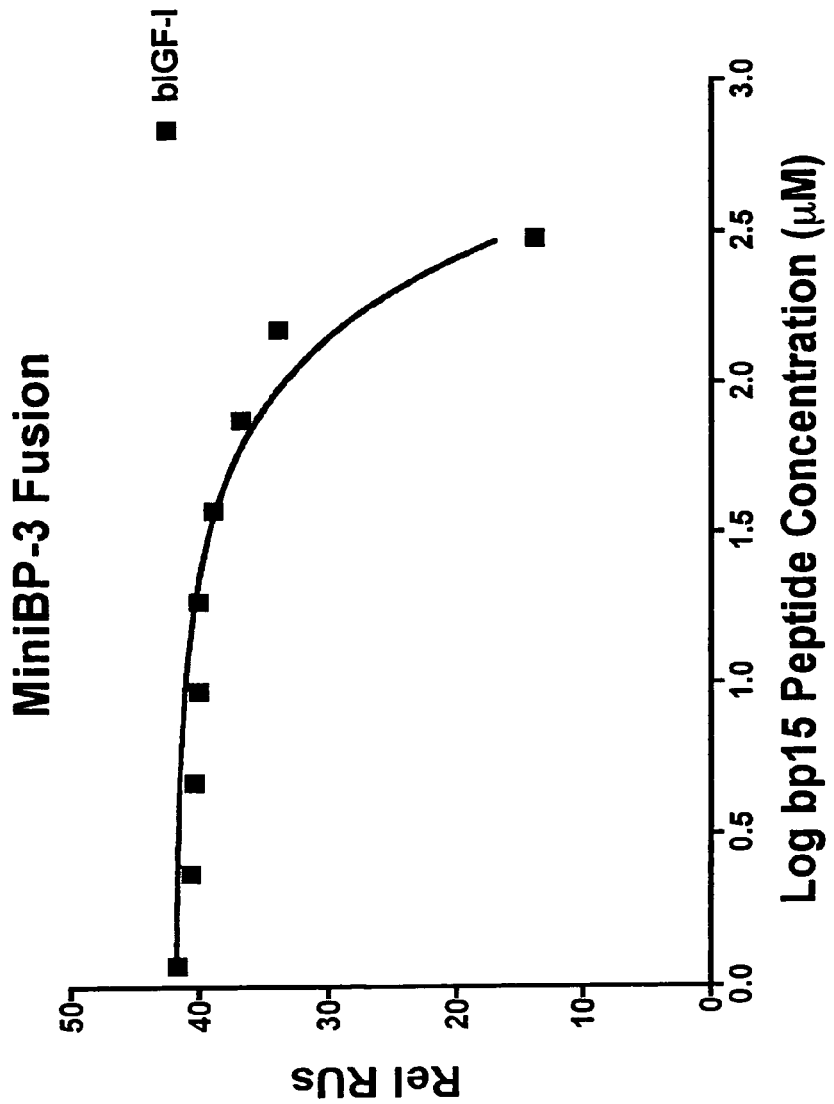
FIG. 8 shows the results of peptide bp 15 (SEQ ID NO:11) competition experiments performed on the BIAcore™ analyzer. A total of 1.17: M to 300:M bp 15 peptide and 1:M miniBP-3 fusion protein was incubated for 1 hour at room temperature before injection over immobilized biotinylated native-sequence human IGF-I.

Peptide bp15 (SEEVCWPVAEWYLCN) (SEQ ID NO:11) was identified by phage display (Lowman et al., *Biochemistry,* 1998, supra). It competes with IGF-I and -II for binding to IGFBP-3 as determined by BIAcore™ analysis as described in Example 1. Therefore, bp15 was tested to see if it would bind to the miniBP-3 fusion. Compare FIGS. 7 and 8 for competitive binding data for bp15 to IGFBP-3 and to the miniBP-3 fusion, respectively.

It can be seen that peptide bp15 does bind to the miniBP-3 fusion, but with reduced affinity compared to wild-type IGFBP-3. Exact affinity was unable to be determined due to lack of saturation.

Discussion:

The miniBP-3 fusion has affinity for IGF-I and IGF-II. This affinity is reduced compared to that of other N-terminal fragments of IGFBP-3. Nevertheless, the miniBP-3 fusion contains at least part of the bp15 peptide-binding site. N-terminal fragments of IGFBP3 have also been associated with IGF-independent effects of IGFBP-3. See, for example, Angelloz-Nicoud et al., *Growth Hormone & IGF Research,* 8: 71-75 (1990); Lalou et al., *Endocrinology,* 137 (8): 3206-3212 (1996); Yamanaka et al., *Endocrinology,* 140 (3): 1319-1328 (1999); Maile et al., *Endocrinology,* 140 (9): 4040-4045 (1999); Salahifar et al., *Growth Hormone & IGF Research,* 10: 367-377 (2000); and Bernard et al., *Biochem. Biophys. Res. Comm.,* 293: 55-60 (2002).

Cell-based assays using a fusion protein containing miniBP-3 or an IGFBP-3 fragment can be developed to detect these IGF-independent events. Thus, in experiments performed by Gill et al., *J. Biol. Chem.,* 272: 25602-25607 (1997) and Fowler et al., *Int. J. Cancer,* 88: 448-453 (2000), breast cancer cells are treated with IGFBP-3 for 24 hours prior to the addition of paclitaxel (and IGFBP-3). Although treatment of the cells with IGFBP-3 alone is not sufficient to induce apoptosis, pre-treatment with IGFBP-3 enhances the apoptosis induced by paclitaxel treatment. The miniBP-3 fusion protein, or fragments of IGFBP-3 that bind to IGF-I or IGF-II and fusion proteins thereof, are expected to be useful in this assay instead of wild-type IGFBP-3 if they contain the activity responsible for potentiation of cell death. An advantage of using the fusion protein or fragments is that they are easier to make in large quantities than intact IGFBP-3, as noted above.

Additionally to these apopiosis assays, cell-based assays can be used for IGF-dependent KIRA assays and radiolabeled IGF binding inhibition, because wild-type IGFBP-3 does not inhibit binding on some cells, perhaps, without being limited to any one theory, due to binding to its own receptor. In an exemplary cell-based IGF-1 KIRA assay, a KIRA for measuring the activation of the human type 1 IGF-1 receptor is performed using human MCF-7 cells. Cells are grown overnight in 96-well plates with medium (50:50 F12/DMEM, Gibco). Supernatants are decanted, and stimulation media (50:50 F12/DMEM with 25 mM HEPES and 2.0% BSA) containing either controls (2 nM IGF-I preincubated with wild-type IGFBP-1 or IGFBP-3) or experimental samples (fusion protein containing miniBP-3 preincubated for 30 min. with 2 nM IGF-1) are added. After 15-minute stimulation the cells are lysed, and added to a polyclonal anti-IGF-1R (3B7; Santa Cruz Biotech) coated overnight on immunosorbant plates. Detection ELISA is performed, and the KIRA results would be expected to show about the same inhibition for the fusion protein containing miniBP-3 as, or possibly more inhibition of IGF-I receptor binding than, that seen for wild-type IGFBP-3, and the inhibition is likely to be improved if the miniBP-3 fragment is affinity matured by phage display or other means as would be known to those skilled in the art.

The present invention has of necessity been discussed herein by reference to certain specific methods and materials. It is to be understood that the discussion of these specific methods and materials in no way constitutes any limitation on the scope of the present invention, which extends to any and all alternative materials and methods suitable for accomplishing the objectives of the present invention.

What is claimed is:

1. A method for determining apoptotic activity of native-sequence human IGFBP-3 in a cell-based assay comprising:
   a) contacting cells with native-sequence human IGFBP-3 and determining apoptosis of the cells,
   b) contacting cells with native-sequence human IGFBP-3 and with a fusion protein comprising a peptide linked to an IGFBP-3 fragment that binds to IGF-I or IGF-II, and determining apoptosis in the cells, and
   c) comparing the cell apoptosis in steps a) and b) and determining if the presence of said fusion protein affects the apoptosis induced by native-sequence human IGFBP-3.

2. The method of claim 1 wherein the activity is independent of IGF-I.

3. A method for determining apoptotic activity of native-sequence human IGF-I in a cell-based assay comprising:

a) contacting cells with native-sequence human IGF-I and determining apoptosis of the cells,
b) contacting cells with native-sequence human IGFBP-3 and with a fusion protein comprising a peptide linked to an IGFBP-3 fragment that binds to IGF-I, and determining apoptosis in the cells, and
c) comparing the cell apoptosis in steps a) and b) and determining if the presence of said fusion protein affects the apoptosis induced by native-sequence human IGF-I.

4. A method for determining apoptotic activity of native-sequence human IGF-II in a cell-based assay comprising:
a) contacting cells with native-sequence human IGF-II and determining apoptosis of the cells,
b) contacting cells with native-sequence human IGFBP-3 and with a fusion protein comprising a peptide linked to an IGFBP-3 fragment that binds to IGF-II, and determining apoptosis in the cells, and
c) comparing the cell apoptosis in steps a) and b) and determining if the presence of said fusion protein affects the apoptosis induced by native-sequence human IGF-II.

5. A method for determining apoptotic activity of a receptor agonist of a native-sequence human IGF-I in a cell-based assay comprising:
a) contacting cells with said receptor agonist of native-sequence human IGF-I and determining apoptosis of the cells,
b) contacting cells with native-sequence human IGFBP-3 and with a fusion protein comprising a peptide linked to an IGFBP-3 fragment that binds to IGF-I, and determining apoptosis in the cells, and
c) comparing the cell apoptosis in steps a) and b) and determining if the presence of said fusion protein affects the apoptosis induced by said receptor agonist of native-sequence human IGF-I.

6. A method for determining apoptotic activity of a receptor agonist of a native-sequence human IGF-II in a cell-based assay comprising:
a) contacting cells with said receptor agonist of native-sequence human IGF-II and determining apoptosis of the cells,
b) contacting cells with native-sequence human IGFBP-3 and with a fusion protein comprising a peptide linked to an IGFBP-3 fragment that binds to IGF-II, and determining apoptosis in the cells, and
c) comparing the cell apoptosis in steps a) and b) and determining if the presence of said fusion protein affects the apoptosis induced by said receptor agonist of native-sequence human IGF-I.

7. The method of claim 1, 3, 4, 5, or 6 wherein the peptide of the fusion protein is SEQ ID NO:10.

8. The method of claim 1, 3, 4, 5, or 6 wherein the IGFBP-3 fragment is a fragment of residues 47 to 99 of native-sequence human IGFBP-3 (SEQ ID NO:1).

9. The method of claim 1, 3, 4, 5, or 6 wherein the method is an IGF-dependent KIRA phosphorylation method.

* * * * *

SEQUENCE LISTING

<160> NUMBER OF SEQ ID NOS: 22

<210> SEQ ID NO 1
<211> LENGTH: 264
<212> TYPE: PRT
<213> ORGANISM: Homo sapiens

<400> SEQUENCE: 1

Gly Ala Ser Ser Gly Gly Leu Gly Pro Val Val Arg Cys Glu Pro

```
               1               5              10              15
Cys Asp Ala Arg Ala Leu Ala Gln Cys Ala Pro Pro Ala Val
                    20              25              30

Cys Ala Glu Leu Val Arg Glu Pro Gly Cys Gly Cys Cys Leu Thr
                    35              40              45

Cys Ala Leu Ser Glu Gly Gln Pro Cys Gly Ile Tyr Thr Glu Arg
                    50              55              60

Cys Gly Ser Gly Leu Arg Cys Gln Pro Ser Pro Asp Glu Ala Arg
                    65              70              75

Pro Leu Gln Ala Leu Leu Asp Gly Arg Gly Leu Cys Val Asn Ala
                    80              85              90

Ser Ala Val Ser Arg Leu Arg Ala Tyr Leu Leu Pro Ala Pro Pro
                    95             100             105

Ala Pro Gly Asn Ala Ser Glu Ser Glu Glu Asp Arg Ser Ala Gly
                   110             115             120

Ser Val Glu Ser Pro Ser Val Ser Ser Thr His Arg Val Ser Asp
                   125             130             135

Pro Lys Phe His Pro Leu His Ser Lys Ile Ile Ile Ile Lys Lys
                   140             145             150

Gly His Ala Lys Asp Ser Gln Arg Tyr Lys Val Asp Tyr Glu Ser
                   155             160             165

Gln Ser Thr Asp Thr Gln Asn Phe Ser Ser Glu Ser Lys Arg Glu
                   170             175             180

Thr Glu Tyr Gly Pro Cys Arg Arg Glu Met Glu Asp Thr Leu Asn
                   185             190             195

His Leu Lys Phe Leu Asn Val Leu Ser Pro Arg Gly Val His Ile
                   200             205             210

Pro Asn Cys Asp Lys Lys Gly Phe Tyr Lys Lys Lys Gln Cys Arg
                   215             220             225

Pro Ser Lys Gly Arg Lys Arg Gly Phe Cys Trp Cys Val Asp Lys
                   230             235             240

Tyr Gly Gln Pro Leu Pro Gly Tyr Thr Thr Lys Gly Lys Glu Asp
                   245             250             255

Val His Cys Tyr Ser Met Gln Ser Lys
                   260

<210> SEQ ID NO 2
<211> LENGTH: 4
<212> TYPE: PRT
<213> ORGANISM: Artificial sequence
<220> FEATURE:
<223> OTHER INFORMATION: Sequence is synthesized

<400> SEQUENCE: 2

Asp Leu Val Asp
 1

<210> SEQ ID NO 3
<211> LENGTH: 4
<212> TYPE: PRT
<213> ORGANISM: Artificial sequence
<220> FEATURE:
<223> OTHER INFORMATION: Sequence is synthesized

<400> SEQUENCE: 3

Asp Glu Met Asp
 1
```

```
<210> SEQ ID NO 4
<211> LENGTH: 4
<212> TYPE: PRT
<213> ORGANISM: Artificial sequence
<220> FEATURE:
<223> OTHER INFORMATION: Sequence is synthesized

<400> SEQUENCE: 4

Asp Glu Met Asp
  1

<210> SEQ ID NO 5
<211> LENGTH: 8
<212> TYPE: PRT
<213> ORGANISM: Artificial sequence
<220> FEATURE:
<223> OTHER INFORMATION: Sequence is synthesized

<400> SEQUENCE: 5

Glu Phe Gly Gly Asp Asp Asp Lys
  1               5

<210> SEQ ID NO 6
<211> LENGTH: 10
<212> TYPE: PRT
<213> ORGANISM: Artificial sequence
<220> FEATURE:
<223> OTHER INFORMATION: Sequence is synthesized

<400> SEQUENCE: 6

Glu Phe Gly Gly Leu Val Pro Arg Gly Ser
  1               5                  10

<210> SEQ ID NO 7
<211> LENGTH: 8
<212> TYPE: PRT
<213> ORGANISM: Artificial sequence
<220> FEATURE:
<223> OTHER INFORMATION: Sequence is synthesized

<400> SEQUENCE: 7

Glu Phe Gly Gly Asp Leu Val Asp
  1               5

<210> SEQ ID NO 8
<211> LENGTH: 8
<212> TYPE: PRT
<213> ORGANISM: Artificial sequence
<220> FEATURE:
<223> OTHER INFORMATION: Sequence is synthesized

<400> SEQUENCE: 8

Glu Phe Gly Gly Asp Glu Met Asp
  1               5

<210> SEQ ID NO 9
<211> LENGTH: 8
<212> TYPE: PRT
<213> ORGANISM: Artificial sequence
<220> FEATURE:
<223> OTHER INFORMATION: Sequence is synthesized

<400> SEQUENCE: 9

Glu Phe Gly Gly Asp Ala Val Asp
  1               5
```

<210> SEQ ID NO 10
<211> LENGTH: 58
<212> TYPE: PRT
<213> ORGANISM: Artificial sequence
<220> FEATURE:
<223> OTHER INFORMATION: Sequence is synthesized

<400> SEQUENCE: 10

```
Val Asp Asn Lys Phe Asn Lys Glu Gln Gln Asn Ala Phe Tyr Glu
 1               5                  10                  15

Ile Leu His Leu Pro Asn Leu Asn Glu Glu Gln Arg Asn Ala Phe
             20                  25                  30

Ile Gln Ser Leu Lys Asp Asp Pro Ser Gln Ser Ala Asn Leu Leu
         35                  40                  45

Ala Glu Ala Lys Lys Leu Asn Asp Ala Gln Ala Pro Lys
             50                  55
```

<210> SEQ ID NO 11
<211> LENGTH: 15
<212> TYPE: PRT
<213> ORGANISM: Artificial sequence
<220> FEATURE:
<223> OTHER INFORMATION: Sequence is synthesized

<400> SEQUENCE: 11

```
Ser Glu Glu Val Cys Trp Pro Val Ala Glu Trp Tyr Leu Cys Asn
 1               5                  10                  15
```

<210> SEQ ID NO 12
<211> LENGTH: 264
<212> TYPE: PRT
<213> ORGANISM: Homo sapiens

<400> SEQUENCE: 12

```
Gly Ala Ser Ser Ala Gly Leu Gly Pro Val Val Arg Cys Glu Pro
 1               5                  10                  15

Cys Asp Ala Arg Ala Leu Ala Gln Cys Ala Pro Pro Pro Ala Val
             20                  25                  30

Cys Ala Glu Leu Val Arg Glu Pro Gly Cys Gly Cys Cys Leu Thr
         35                  40                  45

Cys Ala Leu Ser Glu Gly Gln Pro Cys Gly Ile Tyr Thr Glu Arg
         50                  55                  60

Cys Gly Ser Gly Leu Arg Cys Gln Pro Ser Pro Asp Glu Ala Arg
 65                  70                  75

Pro Leu Gln Ala Leu Leu Asp Gly Arg Gly Leu Cys Val Asn Ala
             80                  85                  90

Ser Ala Val Ser Arg Leu Arg Ala Tyr Leu Leu Pro Ala Pro Pro
         95                  100                 105

Ala Pro Gly Asn Ala Ser Glu Ser Glu Glu Asp Arg Ser Ala Gly
         110                 115                 120

Ser Val Glu Ser Pro Ser Val Ser Ser Thr His Arg Val Ser Asp
         125                 130                 135

Pro Lys Phe His Pro Leu His Ser Lys Ile Ile Ile Ile Lys Lys
         140                 145                 150

Gly His Ala Lys Asp Ser Gln Arg Tyr Lys Val Asp Tyr Glu Ser
         155                 160                 165

Gln Ser Thr Asp Thr Gln Asn Phe Ser Ser Glu Ser Lys Arg Glu
         170                 175                 180

Thr Glu Tyr Gly Pro Cys Arg Arg Glu Met Glu Asp Thr Leu Asn
```

```
                    185                 190                 195
His Leu Lys Phe Leu Asn Val Leu Ser Pro Arg Gly Val His Ile
            200                 205                 210
Pro Asn Cys Asp Lys Lys Gly Phe Tyr Lys Lys Gln Cys Arg
            215                 220                 225
Pro Ser Lys Gly Arg Lys Arg Gly Phe Cys Trp Cys Val Asp Lys
            230                 235                 240
Tyr Gly Gln Pro Leu Pro Gly Tyr Thr Thr Lys Gly Lys Glu Asp
            245                 250                 255
Val His Cys Tyr Ser Met Gln Ser Lys
            260

<210> SEQ ID NO 13
<211> LENGTH: 40
<212> TYPE: DNA
<213> ORGANISM: Artificial sequence
<220> FEATURE:
<223> OTHER INFORMATION: Sequence is synthesized

<400> SEQUENCE: 13
actaaatatg ctagcgccgt agacaacaaa ttcaacaaag                    40

<210> SEQ ID NO 14
<211> LENGTH: 39
<212> TYPE: DNA
<213> ORGANISM: Artificial sequence
<220> FEATURE:
<223> OTHER INFORMATION: Sequence is synthesized

<400> SEQUENCE: 14
atatttagtg aattccttag gcgcctgagc atcatttag                     39

<210> SEQ ID NO 15
<211> LENGTH: 68
<212> TYPE: DNA
<213> ORGANISM: Artificial sequence
<220> FEATURE:
<223> OTHER INFORMATION: Sequence is synthesized

<400> SEQUENCE: 15
actaaataga attcggcggt gatgatgacg acaaagccct gagcgaaggt         50
cagccgtgcg gtatttat                                            68

<210> SEQ ID NO 16
<211> LENGTH: 54
<212> TYPE: DNA
<213> ORGANISM: Artificial sequence
<220> FEATURE:
<223> OTHER INFORMATION: Sequence is synthesized

<400> SEQUENCE: 16
gctcggctgg caacgcagac cgctaccgca acgttcggta taaataccgc         50
acgg                                                           54

<210> SEQ ID NO 17
<211> LENGTH: 66
<212> TYPE: DNA
<213> ORGANISM: Artificial sequence
<220> FEATURE:
<223> OTHER INFORMATION: Sequence is synthesized

<400> SEQUENCE: 17
```

-continued

```
cgttgccagc cgagcccgga tgaagcccgt ccgctgcagg ccctgctgga         50
tggtcgtggt ctgtgc                                              66

<210> SEQ ID NO 18
<211> LENGTH: 68
<212> TYPE: DNA
<213> ORGANISM: Artificial sequence
<220> FEATURE:
<223> OTHER INFORMATION: Sequence is synthesized

<400> SEQUENCE: 18
tatttagtaa gcttctaata ggcacgcaga cggctaacgg cgctggcgtt         50
aacgcacaga ccacgacc                                            68

<210> SEQ ID NO 19
<211> LENGTH: 24
<212> TYPE: DNA
<213> ORGANISM: Artificial sequence
<220> FEATURE:
<223> OTHER INFORMATION: Sequence is synthesized

<400> SEQUENCE: 19
actaaataga attcggcggt gatg                                     24

<210> SEQ ID NO 20
<211> LENGTH: 26
<212> TYPE: DNA
<213> ORGANISM: Artificial sequence
<220> FEATURE:
<223> OTHER INFORMATION: Sequence is synthesized

<400> SEQUENCE: 20
tatttagtaa gcttctaata ggcacg                                   26

<210> SEQ ID NO 21
<211> LENGTH: 39
<212> TYPE: DNA
<213> ORGANISM: Artificial sequence
<220> FEATURE:
<223> OTHER INFORMATION: Sequence is synthesized

<400> SEQUENCE: 21
ggaattcggc ggtgatctgg tggatgccct gagcgaagg                     39

<210> SEQ ID NO 22
<211> LENGTH: 39
<212> TYPE: DNA
<213> ORGANISM: Artificial sequence
<220> FEATURE:
<223> OTHER INFORMATION: Sequence is synthesized

<400> SEQUENCE: 22
ccttcgctca gggcatccac cagatcaccg ccgaattcc                     39
```